(12) United States Patent
Cheng et al.

(10) Patent No.: US 12,057,225 B2
(45) Date of Patent: Aug. 6, 2024

(54) STAMINA MONITORING METHOD AND DEVICE

(71) Applicant: BOMDIC INC., New Taipei (TW)

(72) Inventors: Shih-Heng Cheng, New Taipei (TW); Hsin-Fu Kuo, New Taipei (TW)

(73) Assignee: BOMDIC INC., New Taipei (TW)

( * ) Notice: Subject to any disclaimer, the term of this patent is extended or adjusted under 35 U.S.C. 154(b) by 0 days.

(21) Appl. No.: 18/055,851

(22) Filed: Nov. 16, 2022

(65) Prior Publication Data
US 2023/0072873 A1 Mar. 9, 2023

Related U.S. Application Data

(60) Division of application No. 14/718,104, filed on May 21, 2015, now abandoned, which is a continuation-in-part of application No. 14/460,339, filed on Aug. 14, 2014, now Pat. No. 9,731,184.

(60) Provisional application No. 61/867,229, filed on Aug. 19, 2013.

(51) Int. Cl.
| | |
|---|---|
| *G16H 40/63* | (2018.01) |
| *A61B 5/00* | (2006.01) |
| *A61B 5/0205* | (2006.01) |
| *A61B 5/11* | (2006.01) |
| *A61B 5/145* | (2006.01) |
| *A61B 5/318* | (2021.01) |
| *G16H 50/50* | (2018.01) |
| *G16Z 99/00* | (2019.01) |
| *A61B 5/021* | (2006.01) |
| *A61B 5/024* | (2006.01) |
| *A61B 5/0245* | (2006.01) |

(Continued)

(52) U.S. Cl.
CPC ......... *G16H 40/63* (2018.01); *A61B 5/02055* (2013.01); *A61B 5/1118* (2013.01); *A61B 5/14542* (2013.01); *A61B 5/14546* (2013.01); *A61B 5/318* (2021.01); *A61B 5/4866* (2013.01); *A61B 5/7278* (2013.01); *A61B 5/7405* (2013.01); *A61B 5/742* (2013.01); *A61B 5/7455* (2013.01); *G16H 50/50* (2018.01); *G16Z 99/00* (2019.02); *A61B 5/021* (2013.01); *A61B 5/02405* (2013.01); *A61B 5/0245* (2013.01); *A61B 5/0816* (2013.01); *G16H 20/30* (2018.01)

(58) Field of Classification Search
CPC ........ G16H 40/63; G16H 50/50; G16H 20/30; G16Z 99/00; A61B 5/318; A61B 5/02055; A61B 5/1118; A61B 5/14542; A61B 5/14546; A61B 5/4866; A61B 5/7278; A61B 5/7405; A61B 5/742; A61B 5/7455; A61B 5/021; A61B 5/02405; A61B 5/0245; A61B 5/0816
USPC ............................................... 600/301; 482/8
See application file for complete search history.

(56) References Cited

U.S. PATENT DOCUMENTS

| | | | |
|---|---|---|---|
| 6,605,038 B1 * | 8/2003 | Teller .................... | A61B 5/411 |
| | | | 128/920 |
| 10,600,333 B2 * | 3/2020 | McGibbon ............. | G16H 10/60 |

(Continued)

*Primary Examiner* — Allen Chan
(74) *Attorney, Agent, or Firm* — Chich-Mei Wang

(57) ABSTRACT

The present disclosure provides an exercise assistive device. The present disclosure also provides a method for estimating stamina level and a method for adjusting the method according to a user's anaerobic energy level and aerobic energy level. The present disclosure further provides the several types and applications of the exercise assistive device.

18 Claims, 26 Drawing Sheets

(51) Int. Cl.
 *A61B 5/08* (2006.01)
 *G16H 20/30* (2018.01)

(56) References Cited

U.S. PATENT DOCUMENTS

| | | | | |
|---|---|---|---|---|
| 2005/0054940 | A1* | 3/2005 | Almen | A61B 5/4809 |
| | | | | 600/509 |
| 2006/0252602 | A1* | 11/2006 | Brown | A63B 24/0084 |
| | | | | 482/9 |
| 2008/0033581 | A1* | 2/2008 | Doshi | A63B 71/06 |
| | | | | 700/92 |
| 2008/0214903 | A1* | 9/2008 | Orbach | G16H 40/67 |
| | | | | 705/2 |
| 2011/0021319 | A1* | 1/2011 | Nissila | A61B 5/222 |
| | | | | 482/8 |
| 2011/0066009 | A1* | 3/2011 | Moon | A61B 5/743 |
| | | | | 600/509 |

* cited by examiner

STAMINA MONITORING METHOD AND DEVICE

CROSS-REFERENCES TO RELATED APPLICATIONS

This application is a divisional application of U.S. patent application Ser. No. 14/718,104, filed on May 21, 2015, which is a continuation-in-part of U.S. patent application Ser. No. 14/460,339, filed on Aug. 14, 2014, which claims the benefit of U.S. provisional patent application No. 61/867,229, filed on Aug. 18, 2013, the entirety of which are incorporated herein by reference.

FIELD OF THE INVENTION

The present invention relates generally to an exercise assistive device. More specifically, the present invention relates to an exercise assistive device and method for indicating stamina of a user and providing notification based on certain conditions.

BACKGROUND OF THE INVENTION

Professional athletes, sports enthusiasts or people who like exercise often evaluate their own physical conditions during exercises, and thus configure their own physical strengths in order to complete an exercise or a competition. Typically, people evaluate their own physical conditions and environmental factors before or during an exercise to adjust their workouts. In addition, after an exercise, people record and analyze their physical strengths and endurances as references for the next exercise.

Recently, various types of exercise assistive devices have been developed to assess a user's physical strength in real-time. These devices are capable of providing users with their own physiological signals during exercise and providing the user with exercise history records for browsing after exercise, and sharing the records with social networks. However, the indication of physiological signal, such as heart rate, often cannot be reliably and accurately correlated to the user's physical strength and endurance. Namely, the provision of only the physiological signal is of no or little effect for the user to decide when the used needs to decrease or increase the intensity during the exercise (i.e., when to slow down or speed up during marathon).

In view of the above, what is needed is an exercise assistive device and method which reliably indicates a stamina level of each of the users regardless of the differences of the physical condition among each of the users.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment, and wherein.

In accordance with common practice, the various described features are not drawn to scale and are drawn to emphasize features relevant to the present disclosure. Like reference characters denote like elements throughout the figures and text.

DETAILED DESCRIPTION OF THE INVENTION

Figure 1:
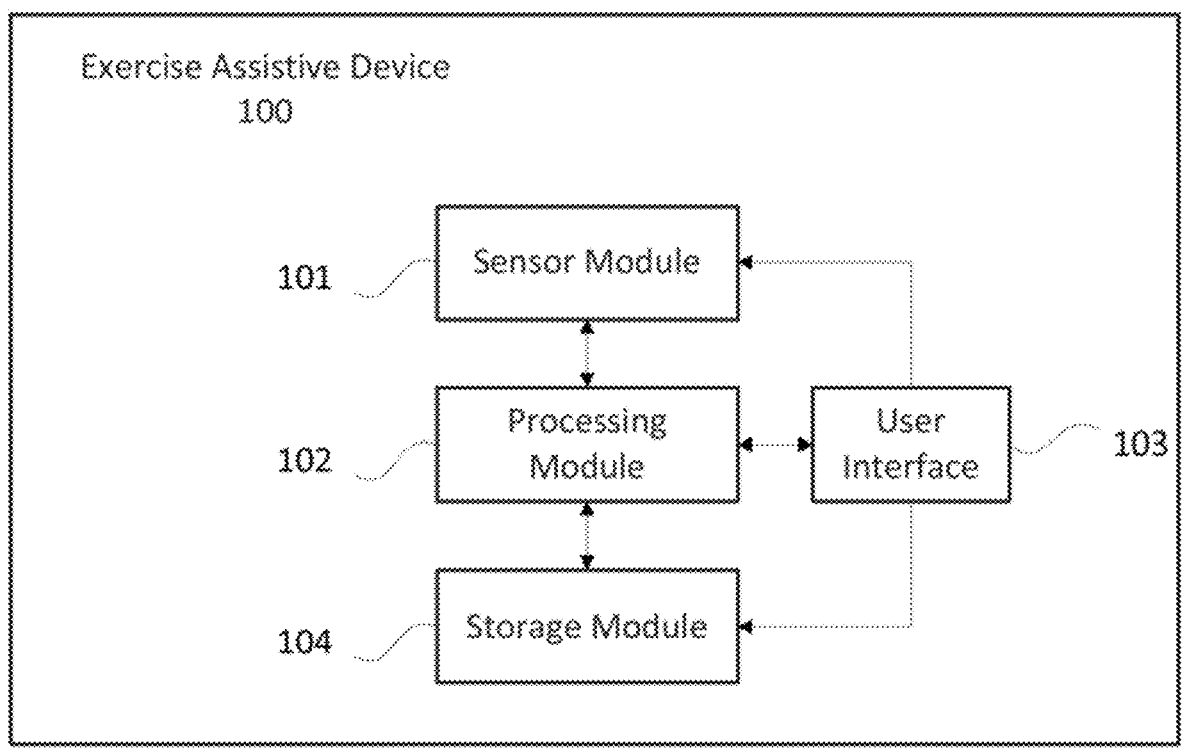
FIG. 1 is a schematic block diagram of an exercise assistive device according to at least one embodiment of the present invention.

The present invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

It will be understood that the term "and/or" includes any and all combinations of one or more of the associated listed items. It will also be understood that, although the terms first, second, third etc. may be used herein to describe various elements, components, regions, parts and/or sections, these elements, components, regions, parts and/or sections should not be limited by these terms. These terms are only used to distinguish one element, component, region, part or section from another element, component, region, layer or section. Thus, a first element, component, region, part or section discussed below could be termed a second element, component, region, layer or section without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The description will be made as to the embodiments of the present invention in conjunction with the accompanying drawings in FIGS. 1-18. Reference will be made to the drawing figures to describe the present invention in detail, wherein depicted elements are not necessarily shown to scale and wherein like or similar elements are designated by same or similar reference numeral through the several views and same or similar terminology.

FIG. 1 is a schematic block diagram of an exercise assistive device (also known as stamina monitoring device) according to at least one embodiment of the present invention.

Referring to FIG. 1, the exercise assistive device 100 includes a sensor module 101, a processing module 102, a user interface 103 and a storage module 104.

The sensor module 101 includes at least one sensor for sensing and measuring physiological signals of the user. For example, the physiological signal comprises at least one of the following: EKG signal, pulse, body temperature, and blood pressure. The body composition may comprise percentages of fat, bone, water and muscle in human bodies.

The processing module 102 is hardware such as a microcontroller or a microprocessor with auxiliary circuits that carries out the instructions of a computer program by performing the basic arithmetical, logical, and input/output operations of the exercise assistive device.

The user interface 103 comprises at least one output unit and/or at least one input unit, or any combination thereof. The output can be a display, a vibrating component or a speaker, or any combination thereof for stating the user's stamina level during or after the exercise of a user. The input can be any human-machine interface such as a touch-panel, a voice receiver or a button that is capable of receiving biological information from the user, such as height, weight, age, gender and so forth. In addition, the user interface 103 can be adapted to send information directly to the sensor module 101, the processing module 102 or the storage module 104. The inputted information may be processed by the processing module 102 and send to the output for the user to know the user's current body condition. For example, BMI value, etc.

The storage module 104 can be any type of disk or memory for storing information from the sensor module 101, the processing module 102 or the user interface 103. For example, the stored information can be activity history or biological information of the user, and the aforementioned information can be used to calculate the user's stamina level and can be used to calculate the user's initial stamina category, since the activity history or the biological information can be used to calculate a base blood lactate acid concentration, a base heart rate, a base oxygen intake rate, or any combination thereof that associates with a rest state of the user.

It should be noticed that the term, stamina, refers to the ability of an organism to exert itself and remain active for a period of time. Furthermore, the concept of the stamina level and the stamina category will be brought out in the following paragraphs.

Referring back to FIG. 1, the processing module 102 receives the physiological signal from the sensor module 101 and processes based on the physiological signal and the instructions stored in the storage module 104, and provides processed information as results to the user interface 103. In addition, the processing module 102 can also receive instructions from the user interface 103 as input and carries out the instructions with or without the information stored in the storage module 104, and provides commands to operate the sensor module 101.

The sensor module 101, the processing module 102, the user interface 103 and the storage module 104 can be configured with wired or wireless connection. The wired connection can be any type of physical contact, for example, an electric cable or conduct lines on printed circuit board. The wireless connection can be any type of wireless transmission, such as WiFi, Bluetooth, or radio frequency assisted transmission.

Figure 2A:
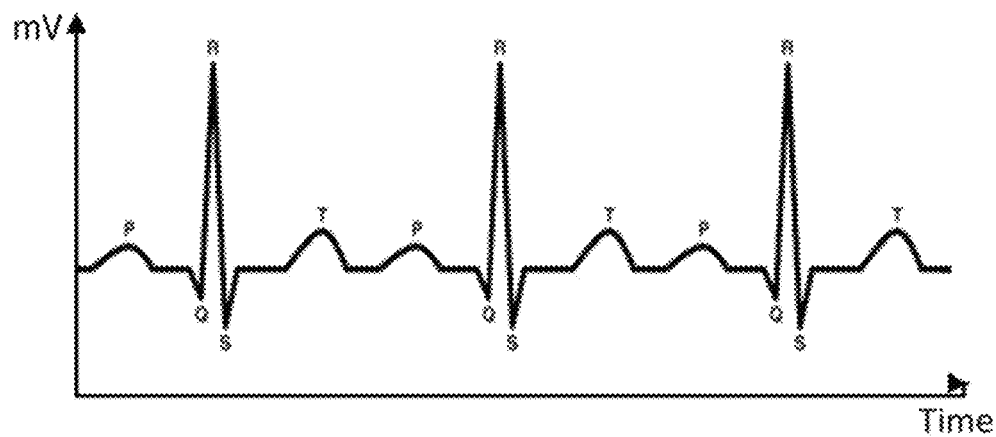
FIGS. 2A and 2B are schematic illustrations of heart waveform created by an EKG signal or by a signal detected from an optical sensor, respectively, according to at least one embodiment of the present invention.
Figure 2B:
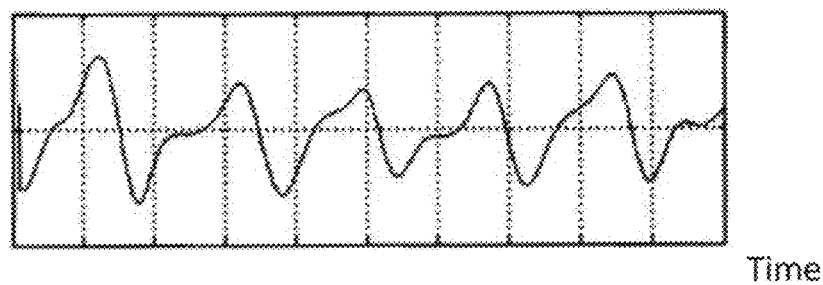

FIGS. 2A and 2B are schematic illustrations of heart waveform created by an EKG signal or by a signal detected from an optical sensor, respectively, according to at least one embodiment of the present invention.

Referring to FIG. 2A, in the sensor module 101 of the exercise assistive device 100, the sensor for monitoring heart rate can be an electrocardiography (EKG) sensor. Referring to FIG. 2B, in the sensor module 101 of the exercise assistive device 100, the sensor for monitoring heart rate can be an optical sensor. Since the optical sensor is sensitive to artifacts such as other heart related signals and body movements, which interfere with the actual heart rate signal and reduce the accuracy of the heart rate reading, the EKG sensor is preferred over the optical sensor as the EKG sensor senses P, Q, R, S and T waves from different operational stages of the heart. The artifacts in an EKG signal can be distinguished from the PQRST waves, thus removing the artifacts to provide an accurate heart rate reading. Namely, the heart rate of a user is determined based on the time intervals between specific EKG waves. For example, the time interval between each consequent T wave or R wave corresponds to the time between each heartbeat. In addition, the EKG signal is used to filter noises through the identification of its specific characteristics of waveform, such as T wave, thus preventing taking irrelevant artifacts in to consideration of heart rate calculation.

Figure 3A:
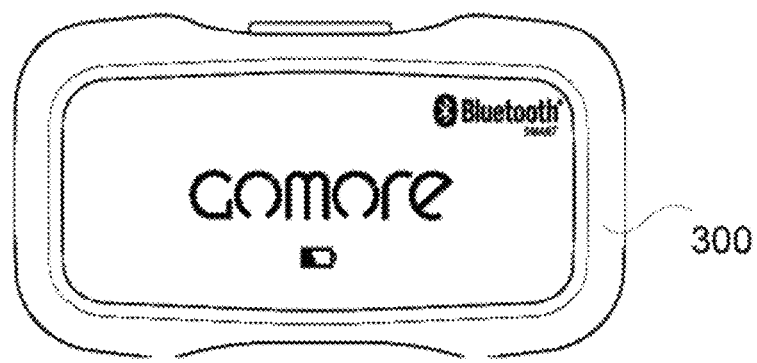
FIGS. 3A to 3C are schematic illustrations of an exemplary exercise assistive device according to one embodiment of the present invention.
Figure 3B:
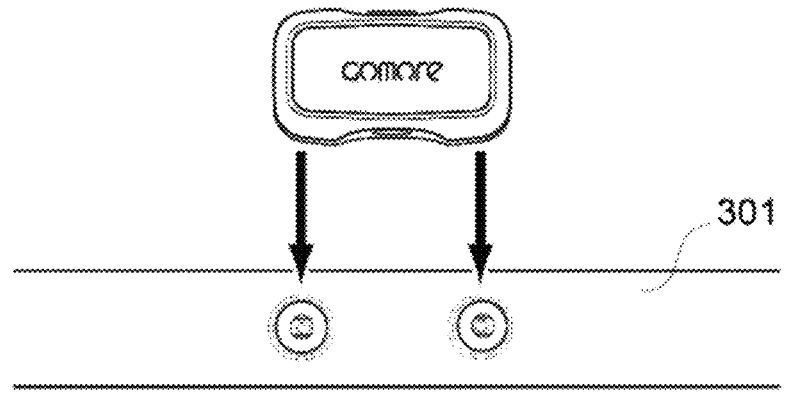
Figure 3C:
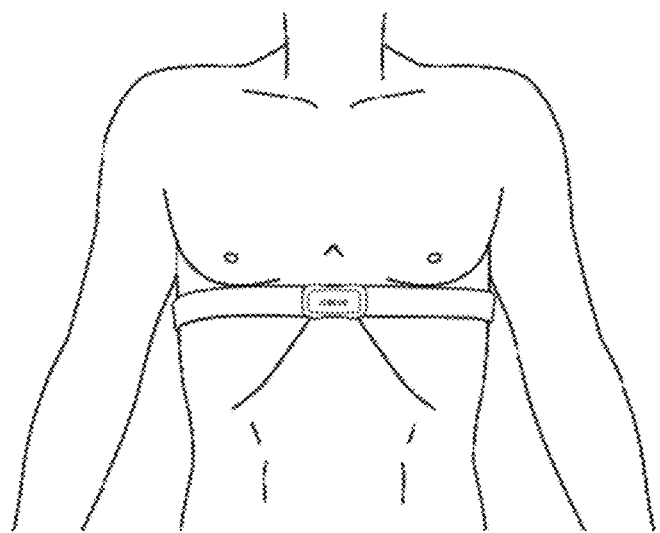

FIGS. 3A to 3C are schematic illustrations of an exemplary exercise assistive device according to one embodiment of the present invention.

Referring to FIGS. 3A to 3C, the exercise assistive device 300 may be a single device having casing that houses at least one of the sensor module 101, the processing module 102, the user interface 103 and the storage module 104. Also, the exercise assistive device 300 may be a single device having casing that houses all of the sensor module 101, the processing module 102, the user interface 103 and the storage module 104. The exercise assistive device 300 may be part of a wearable device to be worn around a human's body part, for example, chest, a wrist, an arm, waist, or a leg, to sense and measure the physiological signals from the body part of the user.

Referring to FIG. 3A, the exercise assistive device 300 comprises an casing that houses a sensor module 101, a processing module 102, a user interface 103 and a storage module 104. Referring to FIG. 3B, the exercise assistive device 300 also comprises a strap 301 (i.e., an elastic band) for strapping the exercise assistive device 300 around a user's chest and positioning the exercise assistive device 100 at the vicinity of the user's heart. In addition, the sensor module 101 of the exercise assistive device 300 may has at least one electrode (i.e., two electrodes connected with the strap) to sense an EKG signal of the user. Referring to FIG. 3C, the exercise assistive device 300 having the strap 301 is worn around a user's chest and thus the EKG signal of the user's heartbeat can be sensed. Furthermore, the exercise assistive device 300 also comprises a vibrating component within the casing for sending vibrating notifications to the user according to the change in the stamina level during the exercise of the user. Again, it should be noticed that the concept of the stamina level will be brought out in the following paragraphs.

Figure 4:
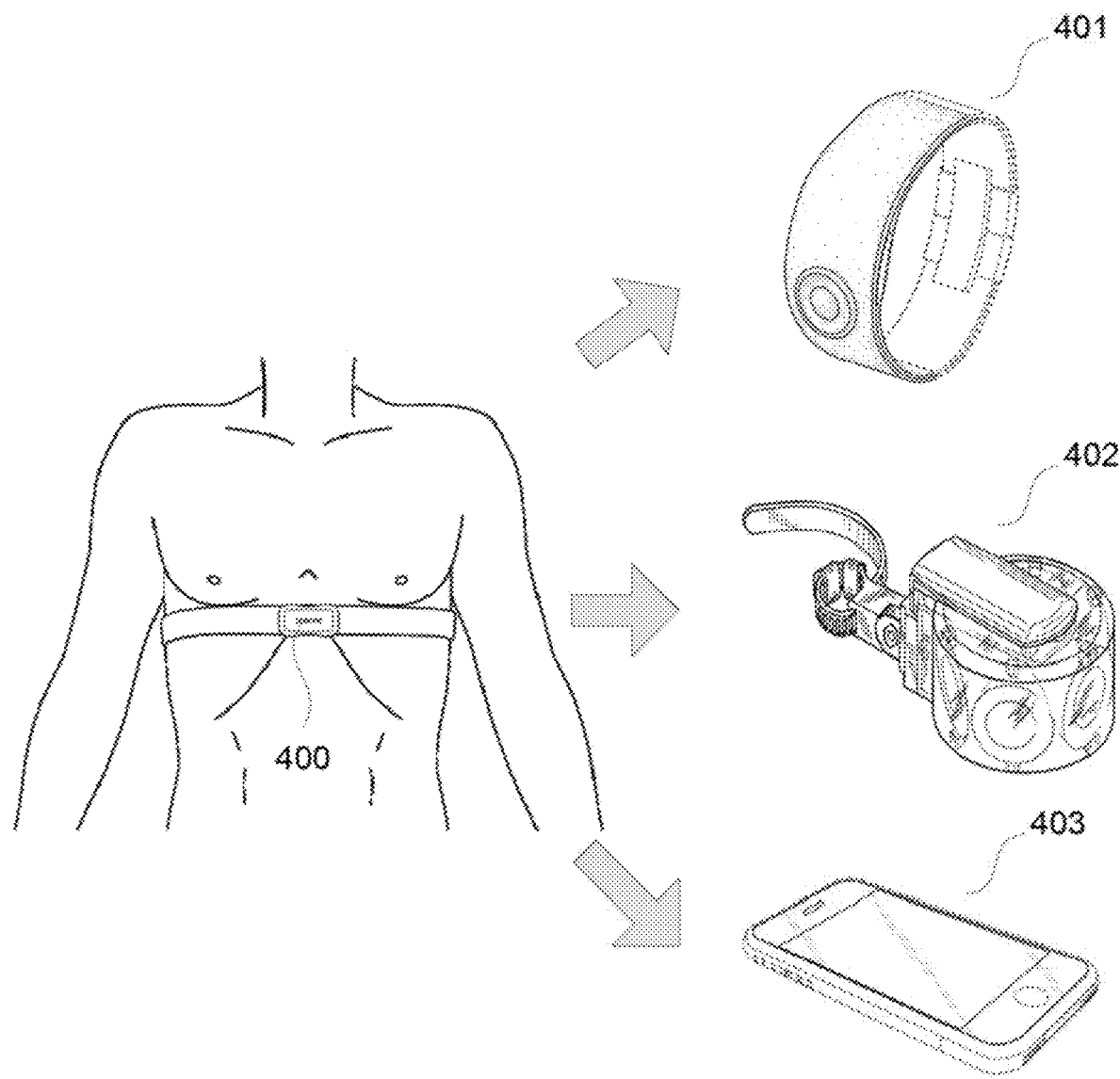
FIG. 4 is a schematic illustration of types of exemplary exercise assistive devices according to another embodiment of the present invention.

FIG. 4 is a schematic illustration of types of exemplary exercise assistive devices according to another embodiment of the present invention.

Referring to FIG. 4, the exercise assistive device 100 may be separate into a first device and a second device. The first device can be configured to wirelessly communicate with the second device. The first device can be a combination of at least one of the sensor module 101, the processing module 102, the user interface 103 or the storage module 104. The second device can be a combination of at least one of the sensor module 101, the processing module 102, the user interface 103 or the storage module 104. Based on the collaboration of the first device and the second device, the function of the original exercise assistive device 100 can be completely operated as well.

The first device can be part of a wearable device 400 to be worn around a human's body part, for example, a chest, a wrist, an arm, waist, or a leg, to sense and measure the physiological signals from the body part. The second device can be a part of an extended device such as a bracelet, a cycling meter, a smart phone, running watches, fitness equipment, or any combination thereof.

To clearly illustrate, the aforementioned extended device may be a bracelet 401 that comprises a user interface that visually illustrates the stamina level of a user in a range, for example from 100% to 0%. The aforementioned extended device may also be an indicator light 402 equipped at the rear of a cycle that illuminates different colors or gleams according to the stamina level of a cyclist. The aforementioned extended device may also be a smart phone 403 that may receive the information, process the information, visually illustrate the stamina level of a user in a range from 100% to 0% (optionally), and even upload the information to the Internet (optionally), such as social network or many types of applications.

Figure 5:
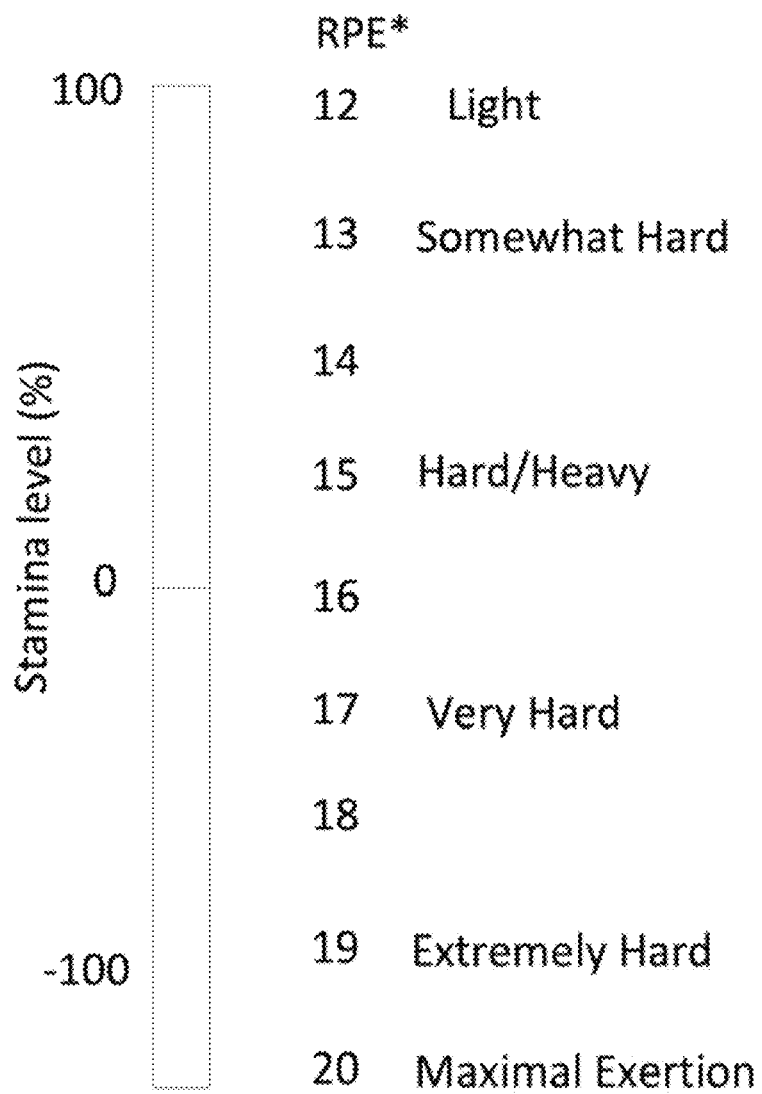
FIG. 5 is a schematic illustration of the mapping concept between stamina level and RPE.

FIG. 5 is a schematic illustration of the mapping concept between stamina level and RPE.

Referring to FIG. 5, a mapping between the stamina level and rating of perceived exertion (RPE) is disclosed. In addition, the type of RPE may be Borg Rating of Perceived Exertion Scale. The stamina level is a measurement resulting from real-time exercise intensity. The stamina level recovers when fatigue level, blood lactate acid concentration (the lactate acid concentration in the blood stream) or real-time exercise loading decreases. On the other hand, the stamina level decreases when fatigue level, blood lactate acid concentration (the lactate acid concentration in the blood stream) or real-time exercise loading increases.

The stamina level can be presented within a certain range, such as 100% to 0%. In addition, the stamina level is at least partially related to the RPE scale linearly or non-linearly. For example, a RPE between 11 and 13 suggests that exercise intensity is being performed at a moderate level by the user of the exercise assistive device 100. That is to say, the user may experience "light" muscle fatigue or breathing, and thus a RPE between 11 and 13 may correspond to a 100% stamina level.

On the other hand, a RPE between 15 and 17 suggests that exercise intensity is being performed at a much higher level by the user of the exercise assistive device 100. That is to say, the user may experience "hard/heavy" muscle fatigue or breathing, and thus a RPE between 15 and 17 may correspond to a 0% stamina level.

To clearly illustrate in an example, the stamina level at 100% maps to a RPE at 12, and the stamina level at 0% maps to a RPE at 16, where the user can recovers from 0% back to 100% stamina level in a time period, such as 8 to 12 minutes preferably.

Moreover, in a perspective that takes heart signal as input of the exercise assistive device 100 as an example, the RPE scale is linearly or nonlinearly proportional to the heart rate, and thus the stamina level is also linearly or nonlinearly proportional to the heart rate. In another example, the stamina level of each user is normalized to a fixed range according to the maximum and minimum heart rate.

It should be noticed that although the aforementioned heart rate is disclosed for mapping and normalizing with the RPE scale and the stamina level, other physiological signal can also be implemented. Also, it should be noticed that the stamina level can be a negative value, and the negative value can be used for the automatic stamina category adjustment calculations, which will be further explained in the following paragraphs.

Figure 6:
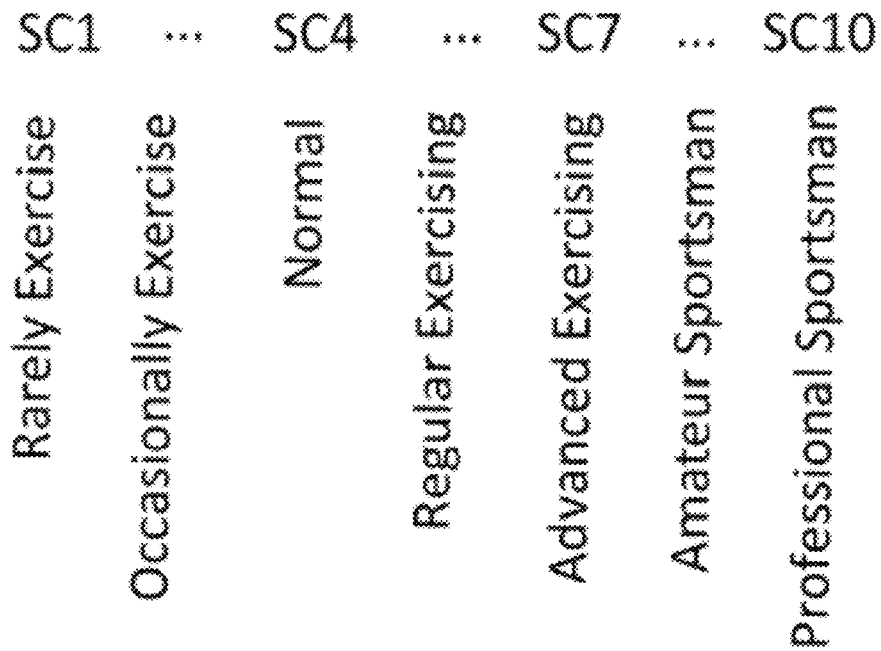
FIG. 6 a schematic illustration of the relationship between exemplary stamina categories and the fitness condition of a user.

FIG. 6 a schematic illustration of the relationship between exemplary stamina categories and the fitness condition of a user.

Referring to FIG. 6, the stamina category is classified into 10 levels, SCI to SC10. Different stamina categories corresponds to different person's physical strength and endurance. For the user that rarely exercises, the stamina category may be initially set to category 1 (SC 1), in the case of a professional athlete, the stamina category may be initially set to category 10 (SC10).

To further elaborate, the stamina category can be determined by the biological information input by the user, and can be modified according to the user's responses during an exercise, more specifically the stamina level change. For example, the exercise assistive device 100 can comprises a default database stored in the storage module 104 that determines the user's stamina category according to the user's biological information such as age, gender, weight, height and the user's exercise routine data (i.e., the information of the stamina category stored in the storage module after the last exercise of the user). The user's biological information or exercise routine data (i.e., the stored stamina category associated with the last exercise of the user) can be inputted by the user through the user interface 103, or can be retrieved from other devices.

No matter what the stamina category is initially set to (i.e., based on biological information of the user or information of a stored stamina category in the exercise assistive device 100), the stamina category for the user is automatically adjusted to a higher stamina category when the stamina level reaches certain thresholds while the user continues with the exercise without severe fatigue, and thus the stamina category adjustment automatically adapts to the user's progression in fitness level. Namely, as the user's physical condition improves, the stamina level maps to the appropriate RPE scale based on the current stamina category of the user, thus reflecting an accurate stamina level. The aforementioned stamina category adjustment can be regarded as an auto-RPE mechanism.

Figure 7:
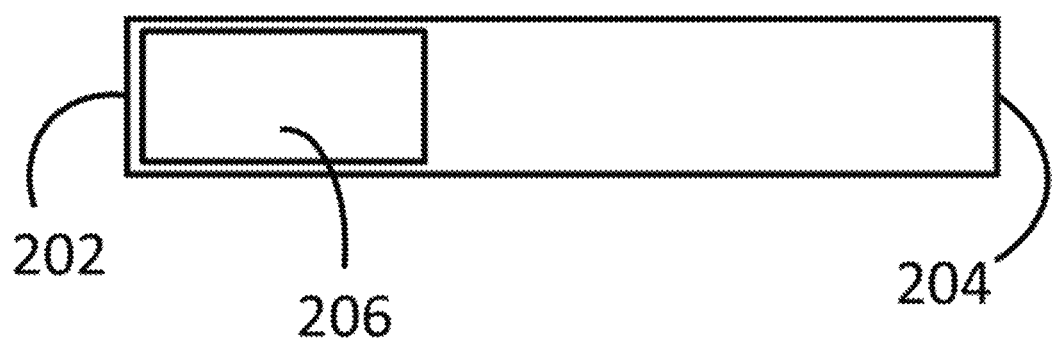
FIG. 7 is a schematic illustration of an exemplary stamina level indicator according to at least one embodiment of the present invention.

FIG. 7 is a schematic illustration of an exemplary stamina level indicator according to at least one embodiment of the present invention.

Referring to FIG. 7, the stamina level is illustrated as a bar, with an upper boundary 204 indicating a 100% stamina level, and a lower boundary 202 indicating a 0% stamina level. Another graphical illustration, for example, a block 206 that is distinguishable from the bar by color, shape or style, represents the current stamina level of the user. The block 206 changes shape, color or style as the current stamina level of the user increases or decreases.

The upper boundary 204 may correspond to an anaerobic threshold, where lactate, more specifically, lactic acid, starts to accumulate in the blood stream due to exercise. The lower boundary 202 may correspond to a certain threshold level for lactic acid concentration, where the user feels exhausted. The threshold level of the lower boundary 202 can be different for each stamina category as each user's endurance to exercise intensity is different. Although the illustration of stamina level is implemented in the form of a bar shape, it is not limited to a bar, and can be implemented with various visual illustrations.

Figure 8:
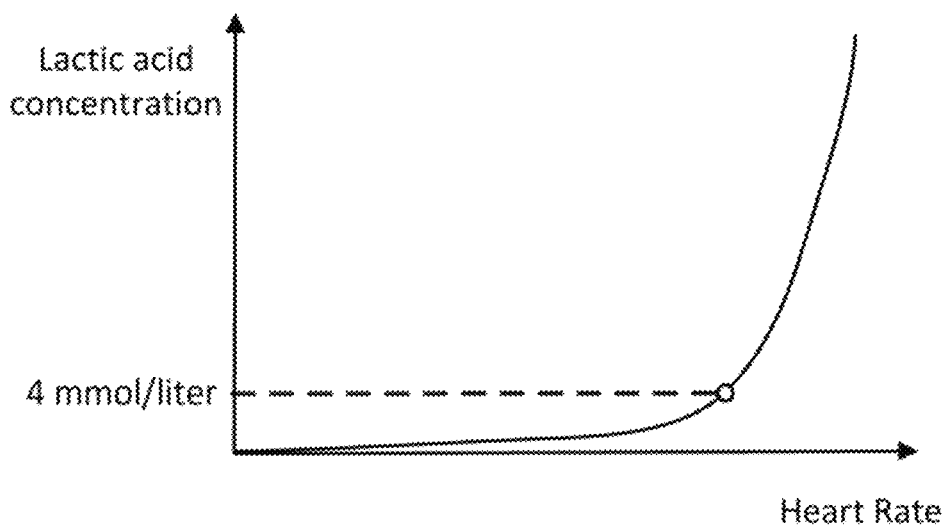
FIG. 8 is a schematic illustration of the correlation between lactic acid concentration and heart rate.

FIG. 8 is a schematic illustration of the correlation between lactic acid concentration and heart rate.

Referring to FIG. 8, the anaerobic threshold for the abovementioned upper boundary 204 is defined as the exercise intensity at which the lactic acid concentration reaches a concentration of 2~6 mmol per liter (at rest it is around 1 mmol per liter).

For example, a 4 mmol per liter of lactate acid concentration is defined as 100% stamina level, and any concentration below 4 mmol per liter is considered as the user's operating at 100% stamina level.

The definition of the aforementioned anaerobic threshold may correlate with approximately 65% to 85% of the maximum heart rate. In addition, the maximum and minimum heart rate of the user is evaluated by age, gender, the rest state of the user, height and weight.

To replace the aforementioned definition of the anaerobic threshold, a certain gradient of the lactic acid concentration and heart rate correlation curve can be defined as 100% stamina level. For example, the 100% stamina level is a point with a gradient value on the curve just before steep incline, which also corresponds approximately to the lactic acid concentration between 2~6 mmol per liter.

It is well known in the art that a lactic acid concentration of 4 mmol per liter is considered as a threshold between aerobic exercise and anaerobic exercise. With aerobic exercise, oxygen is carried through the user's breath to the muscles giving them the energy needed to sustain the effort. With anaerobic exercise, the exercise intensity is high enough to trigger lactic acid formation, which causes discomfort and fatigue at sustained levels.

Figure 9:
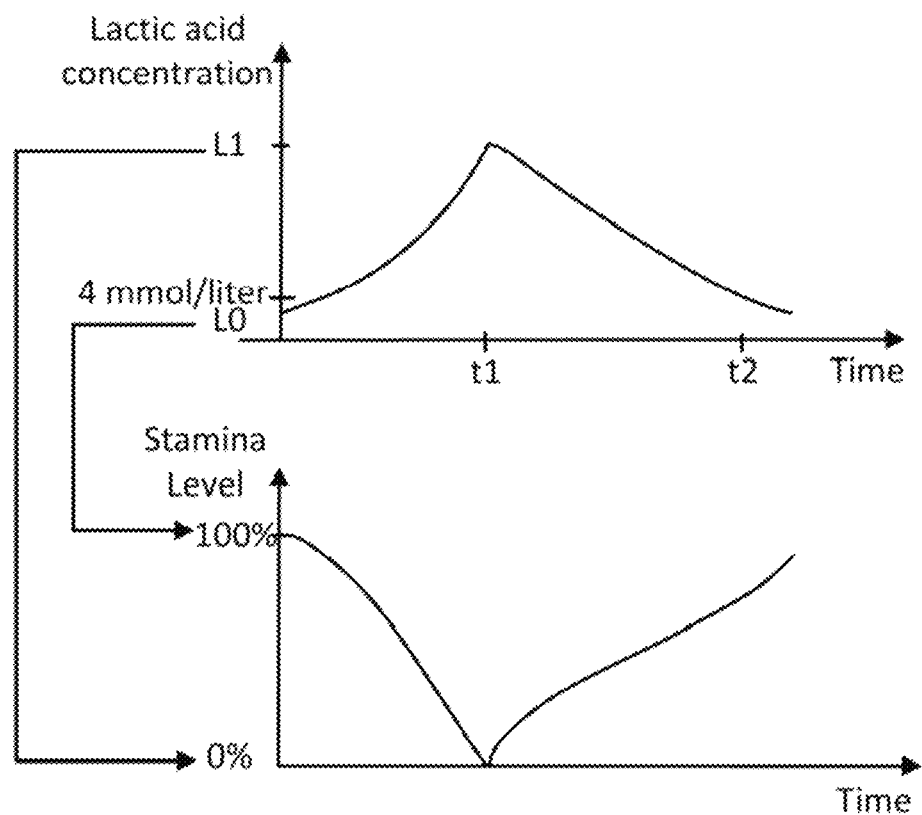
FIG. 9 is a schematic illustration of the changes in lactic acid concentration with respect to the exercise time period of a user and the mapping between lactic acid concentration and stamina level.

FIG. 9 is a schematic illustration of the changes in lactic acid concentration with respect to the exercise time period of a user and the mapping between lactic acid concentration and stamina level.

Referring to FIG. 9, the stamina level of a user with particular stamina category is set to 100% when the lactate acid concentration is at a range of 2~6 mmol per liter. As the user continues with the exercise, the lactate acid concentration increases while the stamina level decreases. Once the lactate acid concentration reaches a threshold, i.e., at L1 lactic acid at t1 time, the user's stamina level reaches substantially 0%. Namely, the user's rate of perceived exertion scale is at approximately 15 to 17, the user may be suggested to choose to decrease the exercise intensity to remove the accumulated lactic acid and thus the stamina level recovers from 0% to 100% during t1 to t2 time frame. It should be noticed that the recovery from 0% to 100% is not necessary, but a recovery from 0% to a certain percentage is better for a user to improve his/her performance during the exercise or competition.

Referring back to FIG. 7, the value for the lower boundary 202 is determined based on the abovementioned t1 to t2 time for the lactic acid concentration to decreases to a predetermined value, for example less than 4 mmol per liter. Regardless of stamina category, the time for different user to fully recovered, for example from 0% to 100% stamina level, is similar, for example, approximately 8 to 12 minutes.

Figure 10:
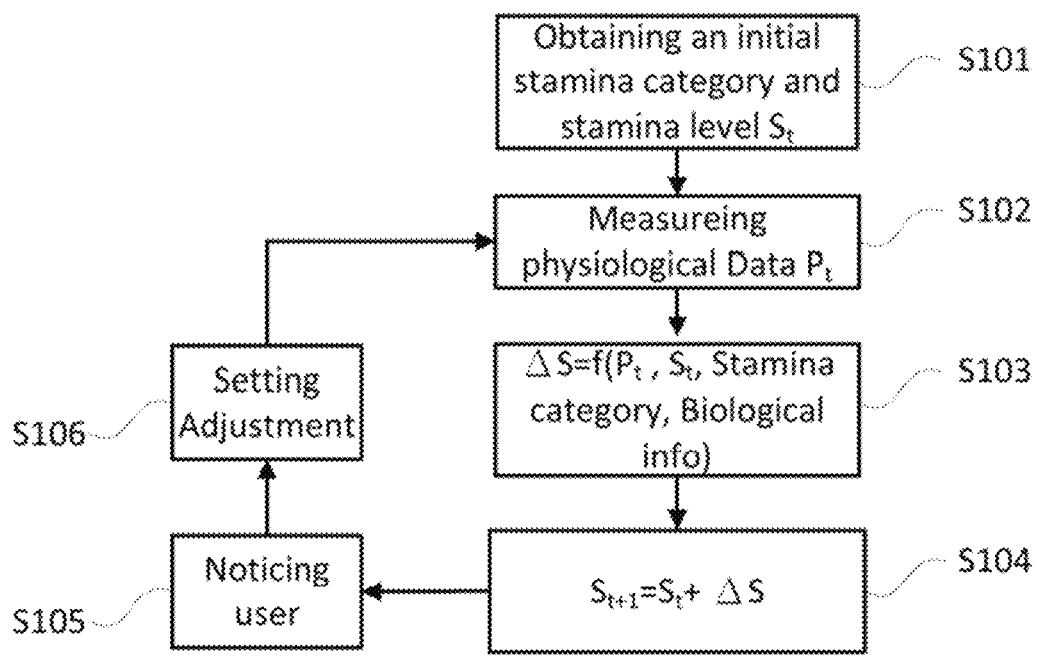
FIG. 10 is a flowchart of a method for estimating stamina level according to at least one embodiment of the present invention.

FIG. 10 is a flowchart of a method for estimating stamina level according to at least one embodiment of the present invention.

Referring to FIG. 10, in step S101, the exercise assistive device 100 first sets the user's initial stamina category and stamina level based on the user's biological information or information of a stored stamina category in the exercise assistive device. The information of the stored stamina category mainly relates to the condition of the user during the last exercise.

In step S102, the physiological information of the user is obtained through the sensor module 101. The physiological information $P_t$ can be current heart rate, activity intensity, oxygen consumption, or any combination thereof.

In step S103, the stamina difference ($\Delta$ S) is calculated based on physiological information ($P_t$), the current stamina level ($S_t$), the initial stamina category and biological information.

Then, In step S104, the subsequent stamina level $S_{t+1}$ is calculated by adding $S_t$ and $\Delta$ S. In step S105, the user is notified when the stamina level decreases or increases to some specific thresholds. In step 106, the initial stamina category can remains at the current level or adjusts to a higher level according to the $S_{t+1}$ (i.e., from SC 3 to SC4).

It should be noticed that the exercise assistive device 100 updates information of the stored stamina category based on the adjustment of the initial stamina category. Also, It should be noticed that the steps S102 to S106 operates iteratively in the exercise assistive device 100, and thus the auto-RPE mechanism remains active during the exercise or competition of the user.

Figure 11:
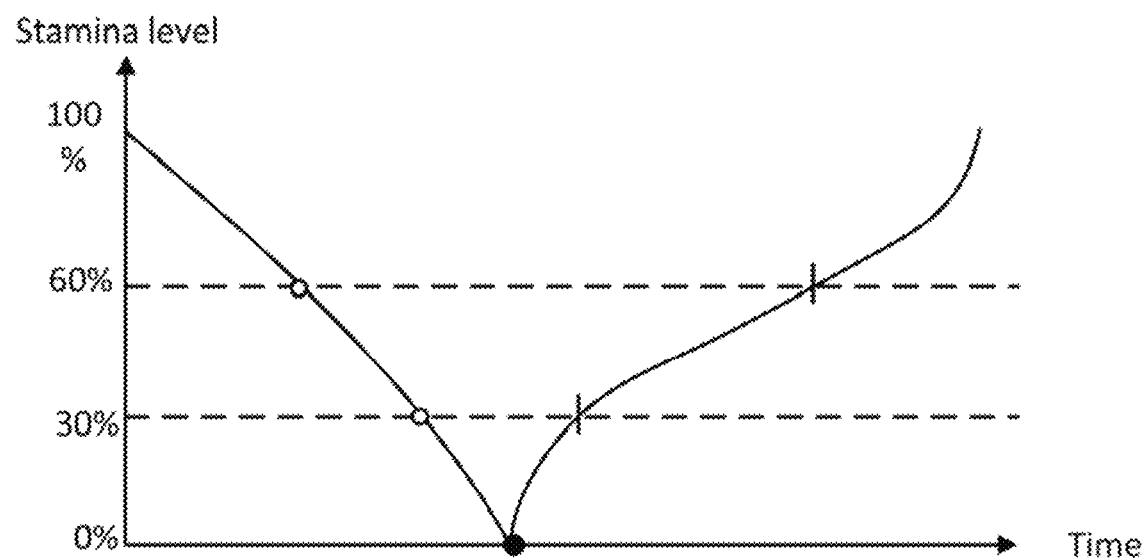
FIG. 11 is a schematic illustration of the exemplary conditions for sending notifications to a user according to at least one embodiment of the present invention.

FIG. 11 is a schematic illustration of the exemplary conditions for sending notifications to a user according to at least one embodiment of the present invention.

Referring to FIG. 11, a notification can be triggered at a stamina level equal to or substantially equal to 0% Vo or other predetermined values no more than 50% or no less than 50%. For example, a notification may be triggered when the stamina level drops to 60%, 30% or 0%. In addition, the notification may also be triggered when the stamina level recovers to 30% or 60%.

The notification may be any form that allows the users to become aware of the notifications, and examples of the notification can be voice, visual or vibrating notifications send out by the user interface 103 notifying the users that exercise intensity should be lower to reduce fatigue or other health related issues. In addition, different types of notifications can be configured for different stamina level. For example, 3 short vibration notifications can be used when the stamina level drops from 60% and then reaches 30% stamina level; a long vibration notification can be used when the stamina level drops from 30% and then reaches 0% stamina level; and 1 short vibration notification can be used when the stamina level rises from 0% and then reaches 30% stamina level or when the stamina level rises from 30% and then reaches 60% stamina level.

Figure 12:
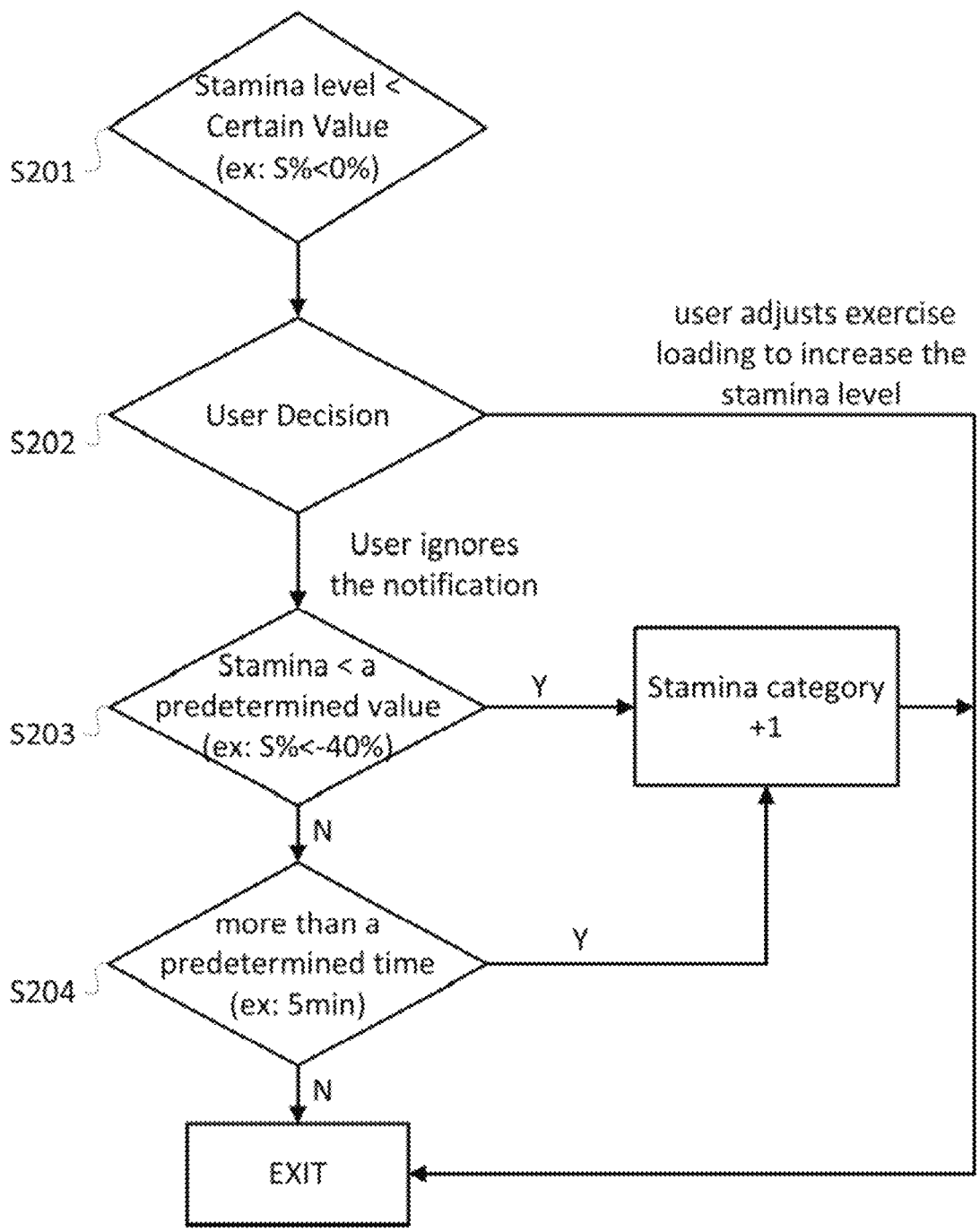
FIG. 12 is a flowchart of a method for adjusting stamina category according to at least one embodiment of the present invention.

FIG. 12 is a flowchart of a method for adjusting stamina category according to at least one embodiment of the present invention.

Referring to FIG. 12, in step S201, when the stamina level drops to a first threshold (or a predetermined value), for example, 0% stamina level, a notification is sent to the user. In step S202, if the user lowers the exercise intensity accordingly and the stamina level starts to recover to above the first threshold, the adjustment ends without modifying the current stamina category.

Then, in step S203, if the user ignores the notification in step S202 and continues with the exercise until the stamina level reaches below a second threshold (or predetermined value), for example, minus 40% stamina level, the stamina category is adjusted to one higher level (i.e., from SC 3 to SC 4).

In step S204, if the user ignores the notification in step S202 and continues with exercise while the stamina level remains between the first and second predetermined value, for example, between 0% and minus 40% stamina level, for more than a first time period (a predetermined time), for example, 4 to 6 minutes, the stamina category is adjust to one higher level (i.e., from SC 3 to SC 4). On the other hand, if the stamina level continuously remains between the first and second predetermined value for less than a first time period (a predetermined time), the adjustment ends without modifying the stamina category.

The stamina level increases or decreases according to each user's exercise intensity during a period of time. Different users with different stamina categories consume different amount of stamina levels during the same period of time. For example, the user with stamina category 3 (SC3) consumes stamina to 0% stamina level faster than the user with stamina category 5 (SC5) assumed the conditions are the same, because the user with SC 5 has more stamina than the user with SC 3.

Thus, if the user's initial stamina category is not appropriate selected, the user may continue with the exercise without feeling severe fatigue after the stamina level reaches 0%, thereby causing sudden situations that fail the exercise or competition. So, the accuracy and effectiveness of the stamina level is based on the appropriate stamina category assigned to the user according to the user's fitness condition. The stamina category can be automatically adjusted to a higher level according to the disclosed adjustment method in FIG. 12.

Figure 13:
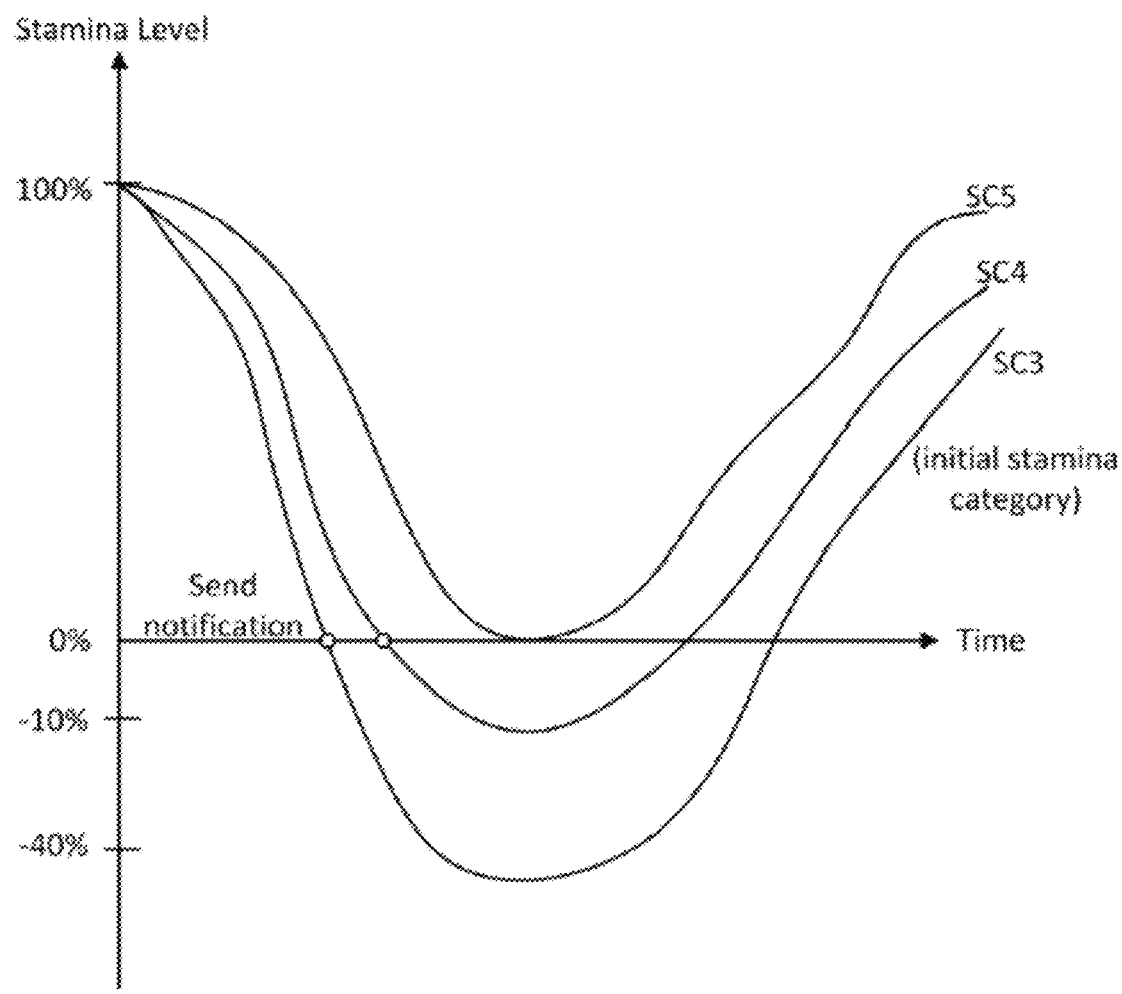
FIG. 13 is a schematic illustration of the exemplary conditions where stamina category can be automatically adjusted in FIG. 12.

FIG. 13 is a schematic illustration of the exemplary conditions where stamina category can be automatically adjusted in FIG. 12.

Referring to FIG. 13, there are two examples of conditions where stamina category can be automatically adjusted. For the user with an initial stamina category of SC3, in a first condition, if the user's stamina level reaches below 0% and the user ignores the notification and continues with the exercise until the stamina level reaches below minus 40%, the user's stamina category is automatically adjusted to SC4.

Then, for the user with an initial stamina category of SC4, in a second condition, if the user's stamina level reaches below 0% and the user ignores the notification and continues with the exercise while the stamina level continuously remains between 0% and minus 10% for more than a first time period (i.e., 5 minutes), the user's stamina category is automatically adjusted to SC5.

Figure 14A:
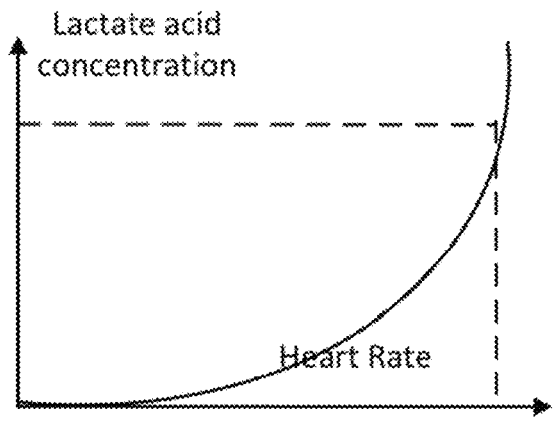
FIGS. 14A and 14B are schematic illustrations of relationship among heart rate, lactate acid concentration and RPE.
Figure 14B:
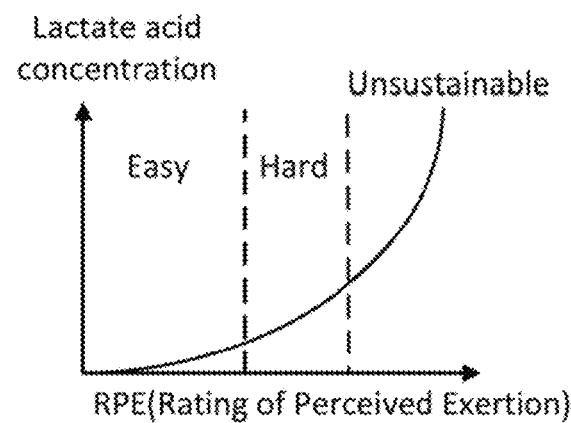
Figure 14C:
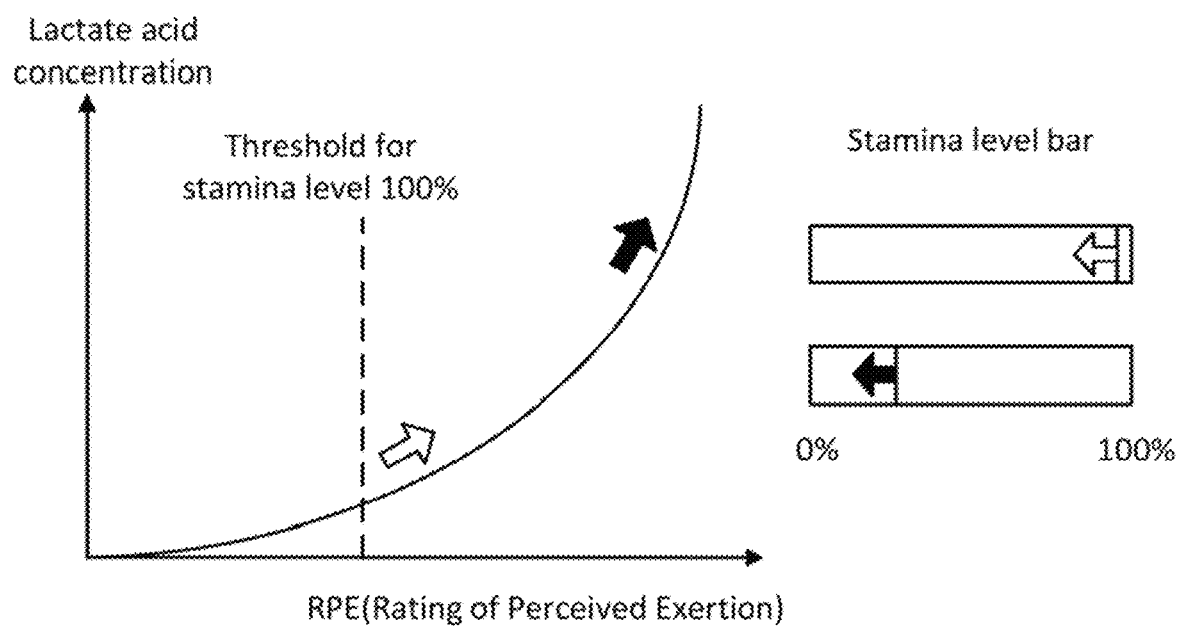
FIG. 14C is the mapping between stamina level and RPE related to lactate acid concentration according to at least one embodiment of the present invention.

FIGS. 14A and 14B are schematic illustrations of relationship among heart rate, lactate acid concentration and RPE, and FIG. 14C is the mapping between stamina level and RPE related to lactate acid concentration according to at least one embodiment of the present invention.

Referring to FIG. 14A, the average heart rate of the user is positively correlated to the lactate acid concentration, which can be approximated with a linear regression model, a non-linear regression model, a piecewise function, other mathematical models or any combination thereof. Thus, the lactate acid concentration associated with the lactate acid accumulated in the blood stream is able to be estimated based on the heart rate of the user.

Referring to FIG. 14B, since the heart rate is positively correlated to or is nearly proportional to the RPE scale, thus the lactate acid concentration is also positively correlated to the RPE scale. When the lactate acid concentration is low, the user experiences "light/easy" in sustaining the exercise effort, and when the lactate acid concentration is high, the user experiences "heavy/hard" or even "unsustainable" in sustaining the exercise effort.

Referring to FIG. 14C, the stamina level is directly correlated to the lactate acid concentration and thus the RPE based on the understanding of FIGS. 14A and 14B. In addition, the stamina level can be represented as a bar-type stamina level indicator as shown in FIG. 7. For example, when the lactate acid concentration reaches above a predetermined threshold in the left side of FIG. 14C, where the stamina level is designated to be 100%, the stamina level indicator starts to decrease as the lactate acid concentration increases following the aforementioned linear or non-linear mathematical models, as illustrated by the white and black arrows in the right side of FIG. 14C.

Figure 15A:
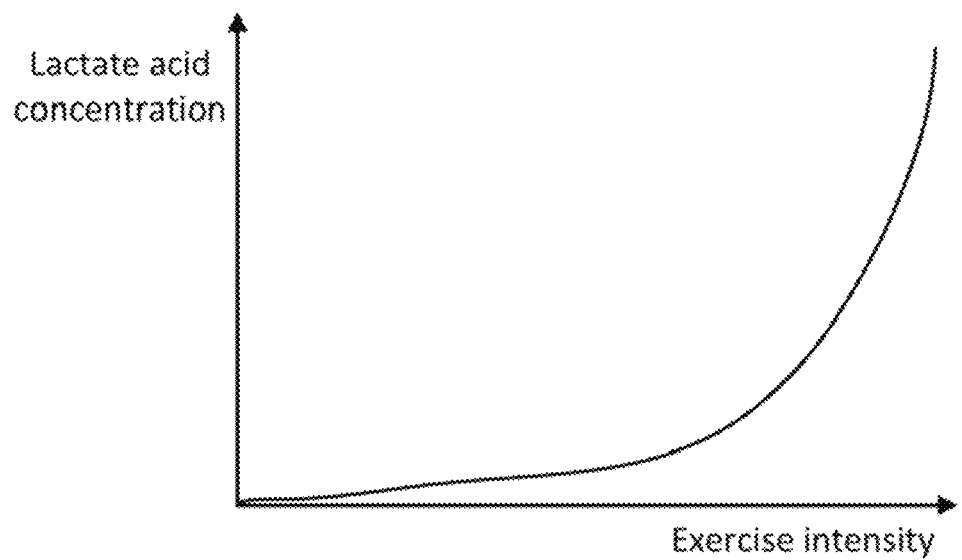
FIGS. 15A and 15B are schematic illustrations of relationship between the lactate acid concentration and exercise intensity or that between the lactate acid concentration and oxygen consumption.
Figure 15B:
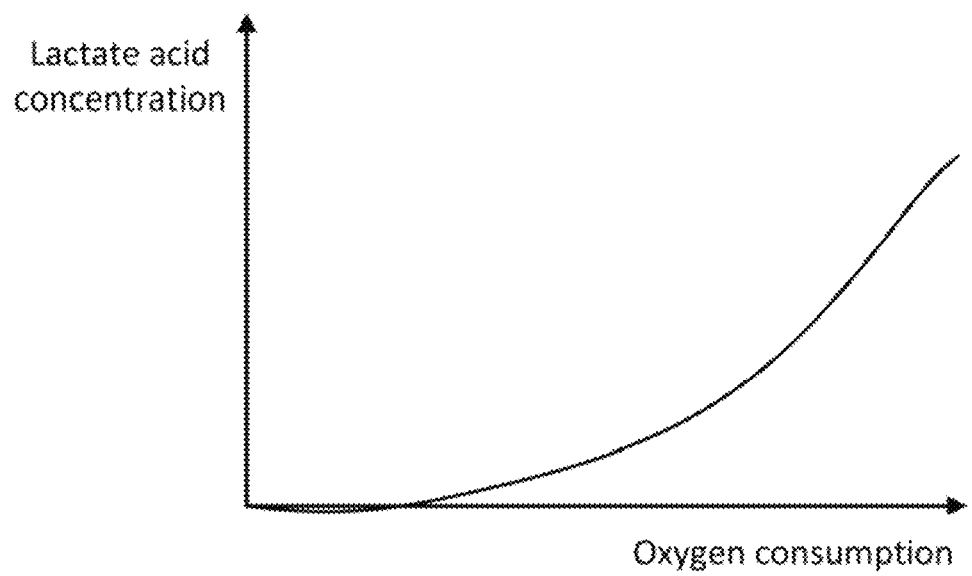

FIGS. 15A and 15B are schematic illustrations of relationship between the lactate acid concentration and exercise intensity or that between the lactate acid concentration and oxygen consumption.

Referring to FIGS. 15A and 15B, the lactate acid concentration associated with the lactate acid accumulated in the blood stream can be estimated based on other physiological signal other than heart rate. For example, the user's exercise intensity or oxygen consumption may be monitored with the sensor module 101, and the aforementioned signals are positively correlated to the lactate acid concentration, which can be approximated with a linear regression model, a non-linear regression model, a piecewise function, other mathematical models, or any combination thereof.

The stamina level can be recorded over a period of time, for example, during an exercise, a race/competition, a challenge and so forth. In addition, the stamina level records can be uploaded to the Internet for further application such as some expressions or interactions in social network. To further elaborate, the stamina level records can be combined with various parameters to fulfill the user's demands for different applications, for example, the stamina level may be combined with at least one of heart rate, velocity, time, map, temperature, humidity, altitude, calorie consumption, exercising efficiency, estimated maximum exercise displacement, or any combination thereof. It should be noticed that the stamina level records may be expressed or exported in real-time or after a period of time.

Figure 16:
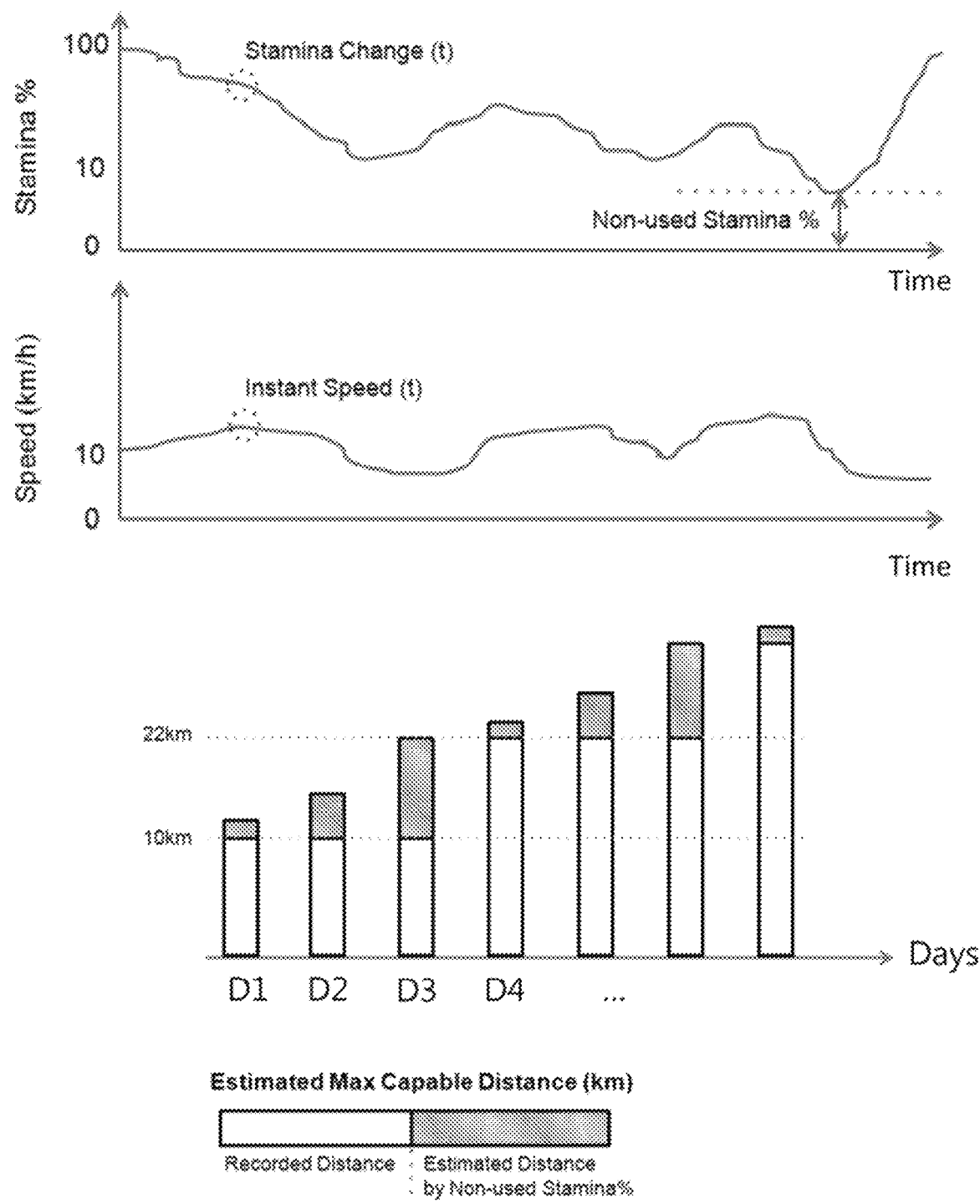
FIG. 16 is a schematic illustration of an exemplary application of estimating a user's maximum exercise distance using the user's stamina level and exercise speed.

FIG. 16 is schematic illustration of an exemplary application of estimating a user's maximum exercise distance using the user's stamina level and exercise speed.

To begin with, the users may refer back to the stamina level record histories to evaluate their stamina level changes over certain distance, speed, terrains, temperature or weather condition, and adjust their speed or route for the next exercise session. The users may also monitor their stamina level changes over the same course for several days or weeks to evaluate their progress in fitness levels.

Referring to FIG. 16, the user's stamina level is correlated to the user's exercising speed over a certain period of time. For example, if a user has completed a 5 kilometer running exercise with 10% stamina level remaining, the exercise assistive device 100 can estimate the total running distance if the user is to used up all 100% stamina level for this exercise.

The additional distance associated with the remaining 10% stamina level may be estimated by multiplying the instant speed of the user with the stamina consumption time, and the aforementioned additional distance refers to an estimated distance by non-used stamina percentage, For example, if the additional distance associated with the remaining 10% stamina level is estimated to be 1 kilometer, the exercise assistive device 100 may notifies the user that a 100% stamina corresponds to a total of 6 kilometer running exercise.

Therefore, the estimated maximum exercise displacement can be used in designing training plans. For example, the user may have a training plan that has different distance targets in the first day and the consequent days. For example, the exercise assistive device 100 shows that the recorded distance exercised by the user is 10 kilometer in Day 1, but the estimated maximum exercise displacement is 11 kilometer since the estimated distance by non-used stamina percentage is 1 kilometer. In Day 3, the estimated maximum exercise displacement reaches to 22 km, and thus the user with the exercise assistive device 100 is ready to practice running at a distance of 22 kilometers in Day 4 under proper evaluation.

It should be noticed that different users with different stamina categories may compare their stamina level records with each other to adjust their exercise loading distribution since the stamina level of each user is normalized to a range of 0% to 100%. In another example, a gym coach can monitor the stamina level of all the members in a class and inform each individual to adjust his/her exercise loading accordingly.

Figure 17:
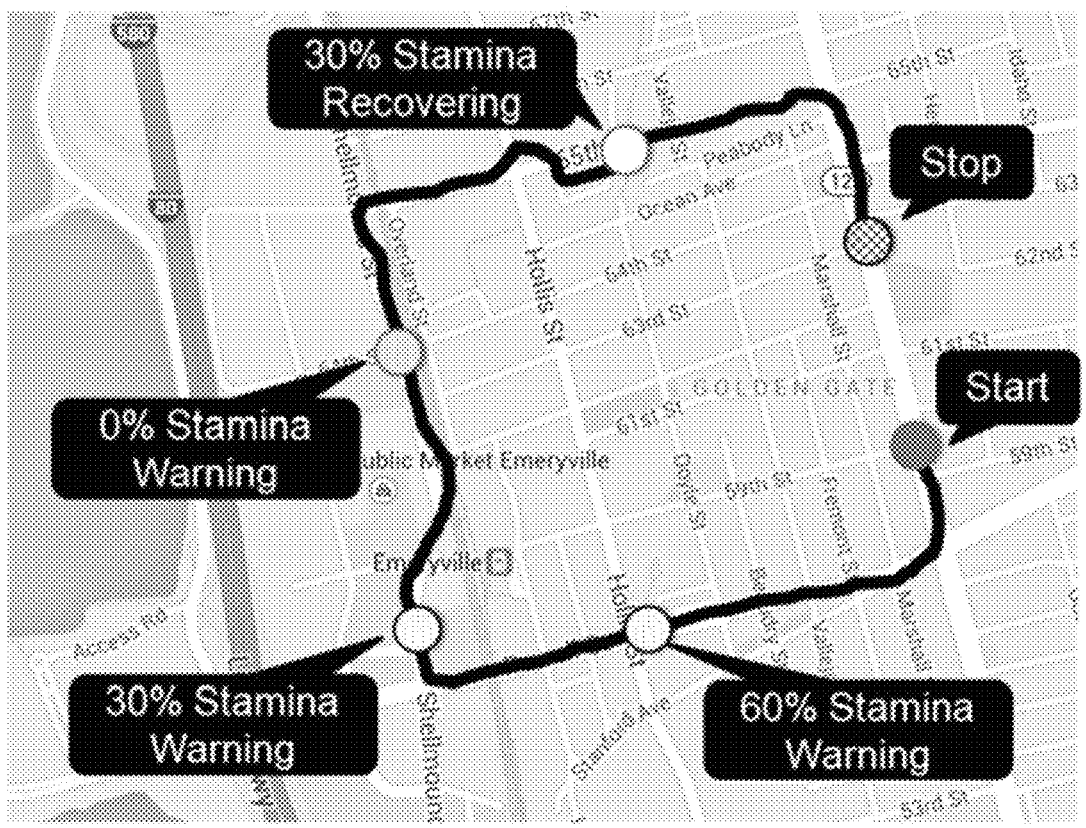
FIG. 17 is a schematic illustration of an exemplary application of outputting the user's stamina level in conjunction with a map.

FIG. 17 is schematic illustration of an exemplary application of outputting the user's stamina level in conjunction with a map.

Referring to FIG. 17, the stamina level records can be utilized with GPS data and correlated with a map to evaluate the locations where most users have dramatic decrease in stamina level, for example, at the top of a steep hill.

The aforementioned information may be beneficial to water or food store owners to evaluate the locations to set up their stores. In addition, the aforementioned information may be combined with the information captured by some specific devices, such as a video recorder or a camera, and thus the user's video feeds along with the user's stamina level can be watched through the Internet.

Figure 18:
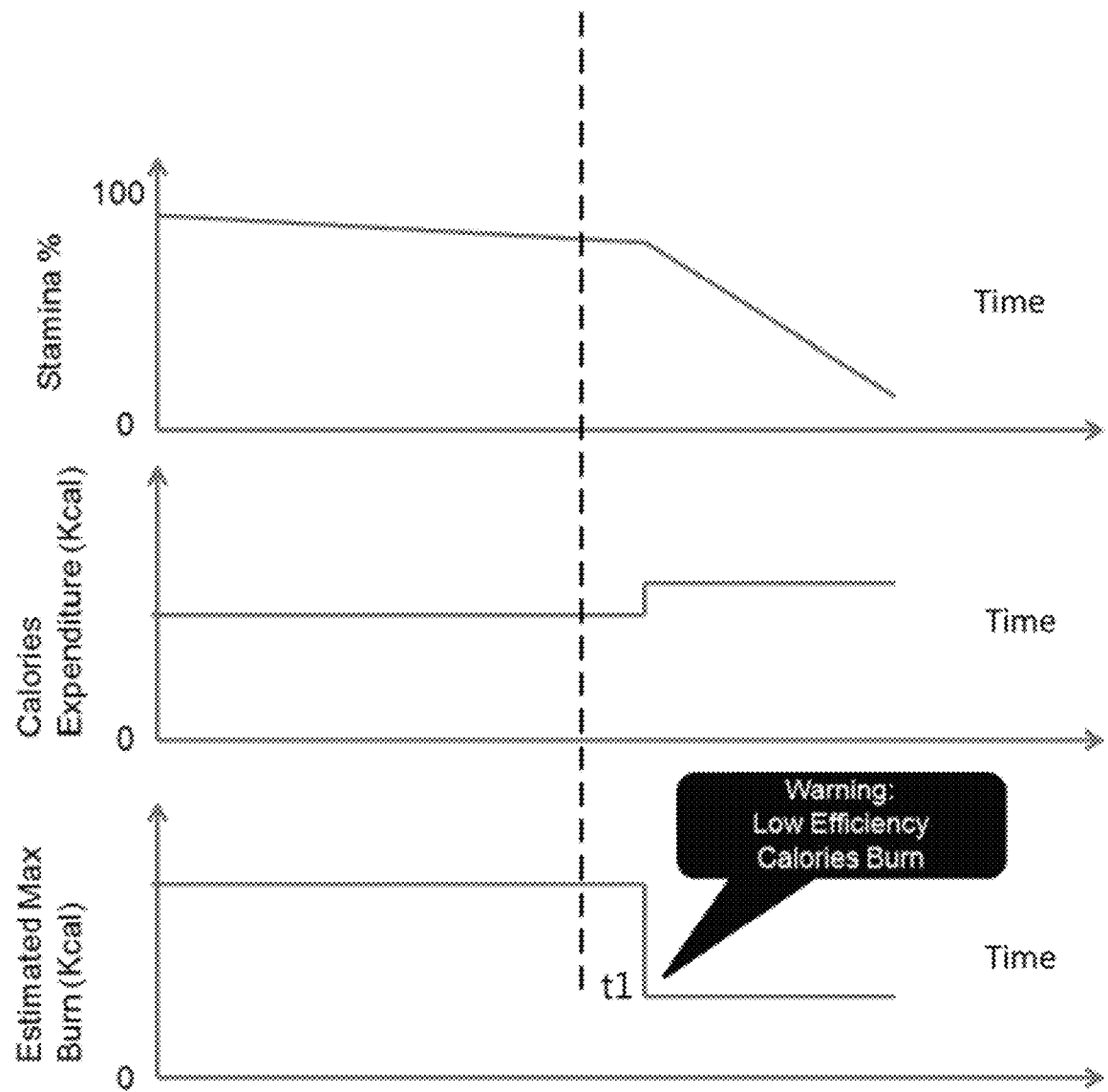
FIG. 18 is a schematic illustration of an exemplary application of estimating a user's calorie consumption by utilizing the user's stamina level.

FIG. 18 is schematic illustration of an exemplary application of estimating a user's calorie consumption by utilizing the user's stamina level.

Referring to FIG. 18, the user's stamina level can be mapped to the user's calorie consumption with mathematical models. For example, if a user is exercising with a steady pace, the steady decrease in the stamina level corresponds to a constant calorie consumption. The total calorie consumption during the exercise may be estimated by multiplying this constant calorie consumption with the total time of this exercise. If the user is to increase the exercise loading at time t1, the calorie consumption becomes higher. However, the user may not be able to sustain with the exercise loading for a long time, and therefore the total calorie consumption may be lower after time t1. If the main goal for the user is to lose weight by maximizing caloric burns, the exercise assistive device is able to illustrate the correlation between the exercise loadings (i.e., the rate of decreasing in the stamina level) with the total calorie consumption, and sends notifications to the user suggesting the appropriate exercise loading.

Figure 19:
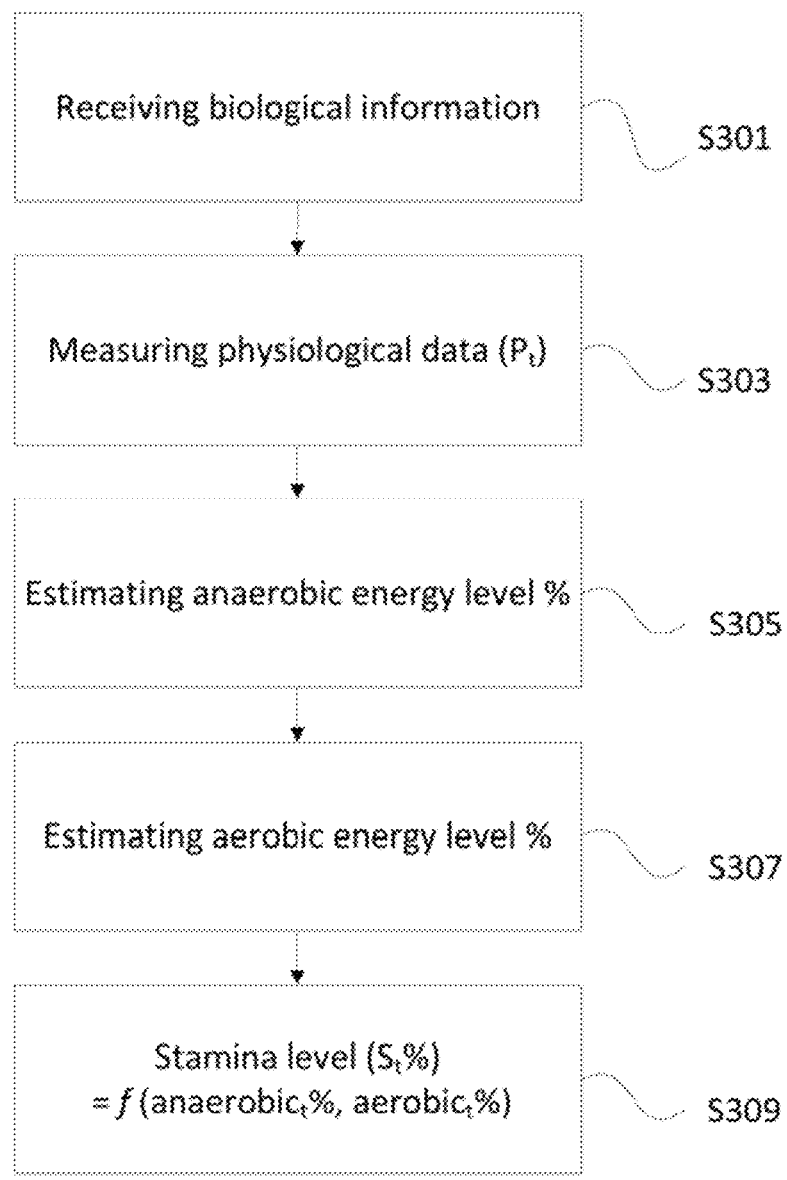
FIG. 19 is a method to estimate stamina level based on physiological data according to one embodiment of the present invention.

FIG. 19 is a method to estimate stamina level based on physiological data according to one embodiment of the present invention.

In one embodiment of the present invention, stamina level is a combination of anaerobic energy level and aerobic energy level, wherein the stamina level is positively correlated to the anaerobic energy level and aerobic energy level that can be estimated by a linear regression model, a non-linear regression model, a piecewise function, other mathematical models or any combination thereof.

Referring to FIG. 19, the following steps may be carried out to estimate stamina level based on physiological data:

S301: Receiving biological information from the user interface 103;

S303: Measuring physiological data ($P_t$) by the sensor module 101;

S305: Estimating anaerobic energy level in percentage by the processing module 102 based on the physiological data ($P_t$);

S307: Estimating aerobic energy level in percentage by the processing module 102 based on the physiological data ($P_t$) and the biological information;

S309: Estimating the stamina level in percentage ($S_t$%) based on the anaerobic energy level and the aerobic energy level in percentage by the processing module 102.

In one embodiment of the present invention, the order of steps S301, S303, S305 and S307 is interchangeable as long as S301 is before S307 and S303 is before both S305 and S307.

In one embodiment of the present invention, the biological information may comprise at least one of the following: height, weight, age, and gender, etc.

In one embodiment of the present invention, the physiological data ($P_t$) may comprise at least one of the following: an EKG signal, heart rate variability, pulse, heart rate, breathing pattern, body temperature, blood glucose, blood pressure, glycogen concentration, and oxygen concentration, etc. Each time the physiological data ($P_t$) is measured, the physiological data ($P_t$) may be either saved in the storage module 104 for later use or be sent to the processing module 102 for estimation of the anaerobic energy and the aerobic energy.

In one embodiment of the present invention, the stamina level ($S_t$%) may be mapped to RPE scale by the processing module 102 and outputted to the user by the user interface 103.

In one embodiment of the present invention, the anaerobic energy level may be correlated to accumulation of lactate acid concentration, and the aerobic energy level may be correlated to extra calorie consumption. In this case, the stamina level ($S_t$%) may be estimated based on the accumulation of lactate acid concentration and the extra calorie consumption using a linear regression model, a non-linear regression model, a piecewise function, other mathematical models or any combination thereof.

Figure 20:
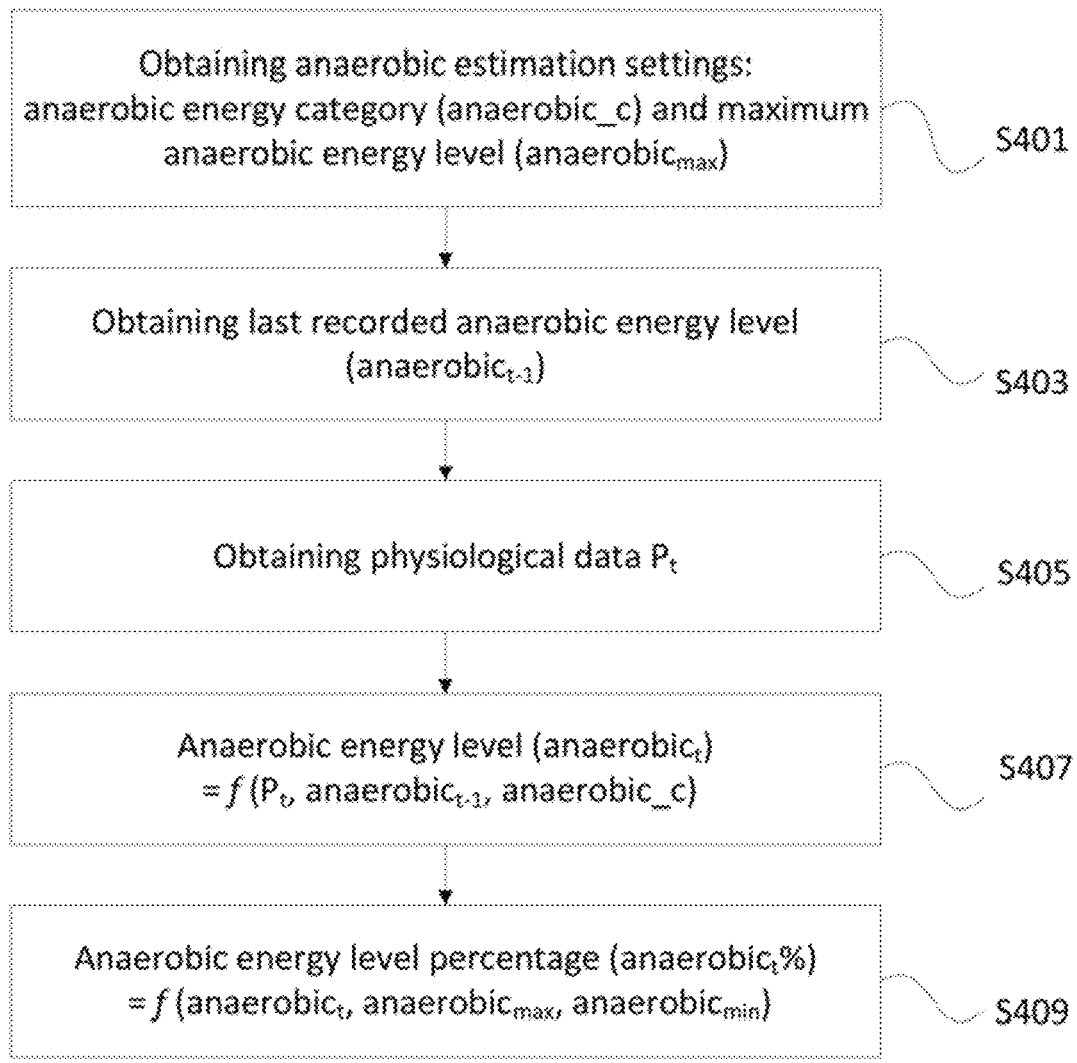
FIG. 20 is a method to estimate anaerobic energy based on physiological data according to one embodiment of the present invention.

FIG. 20 is a method to estimate anaerobic energy based on physiological data according to one embodiment of the present invention, wherein the method is an elaboration of the step S305 in FIG. 19.

Referring to FIG. 20, the following steps may be carried out to estimate the anaerobic energy based on physiological data:

S401: Obtaining anaerobic estimation settings such as anaerobic energy category (anaerobic_c) and maximum anaerobic energy level ($anaerobic_{max}$) from the storage module 104;

S403: Obtaining last recorded anaerobic energy level ($anaerobic_{t-1}$) from the storage module 104;

S405: Obtaining physiological data ($P_t$) from the storage module 104;

S407: Estimating anaerobic energy level ($anaerobic_t$) by the processing module 102 based on the physiological data ($P_t$), the anaerobic estimation settings and the last recorded anaerobic energy level ($anaerobic_{t-1}$);

S409: Calculating anaerobic energy level in percentage ($anaerobic_t$%) by the processing module 102 using the anaerobic energy level ($anaerobic_t$), maximum anaerobic energy level ($anaerobic_{max}$) and a minimum anaerobic energy level ($anaerobic_{min}$).

In one embodiment of the present invention, the order of the step S401, S403 and S405 are interchangeable.

In one embodiment of the present invention, in step S405, the physiological data ($P_t$) may be measured by the sensor module 101 instead of obtained from the storage module 104. Therefore, the method to estimate anaerobic energy may be carried out without relating to the method in FIG. 19.

In one embodiment of the present invention, the anaerobic energy category (anaerobic_c) may be a lactate acid dilution rate or a lactate acid production rate.

In one embodiment of the present invention, the anaerobic energy level may be the accumulation of lactate acid concentration of the user, and the maximum anaerobic energy level ($anaerobic_{max}$) may be a maximum lactate acid concentration that a person can withstand theoretically, wherein the maximum lactate acid concentration may be varied by adjustment to anaerobic estimation settings. For example, a professional athlete may withstand higher lactate acid concentration than a casual runner. In addition, even the same person may withstand different lactate acid concentration. For example, a person stop exercising for a period of time, the person might be only able to withstand lower lactate acid concentration than before. Another example is that a person exercise regularly might be able to withstand higher lactate acid concentration than before. Therefore, the maximum anaerobic energy level ($anaerobic_{max}$) may be pre-configured with a certain value, and be adjusted each time the exercise assistive device 100 estimates the stamina level ($S_t$%). Alternatively, the adjustment may also be carried out after the exercise assistive device 100 is turned off or on by the user. The method of adjustment to anaerobic estimation settings will be introduced later on.

In one embodiment of the present invention, the minimum anaerobic energy level ($anaerobic_{min}$) may be a lactate acid concentration that a user can sustain without increasing the user's lactate acid concentration dramatically while doing exercise. In this case, the minimum anaerobic energy level ($anaerobic_{min}$) may be set to 4 mmol/liter as shown in FIG. 8. The minimum anaerobic energy level ($anaerobic_{min}$) may either be a constant pre-configured in the exercise assistive device 100 as a constant or be inputted by the user using the user interface 103.

In one embodiment of the present invention, the last recorded anaerobic energy level ($anaerobic_{t-1}$) may be a value stored in the storage module 104 from the last estimation of anaerobic energy level, wherein $anaerobic_{t-1}$ may be equal to $anaerobic_{min}$ in the case of first time using the exercise assistive device 100 assuming no exercise has been done by the user.

Figure 21:
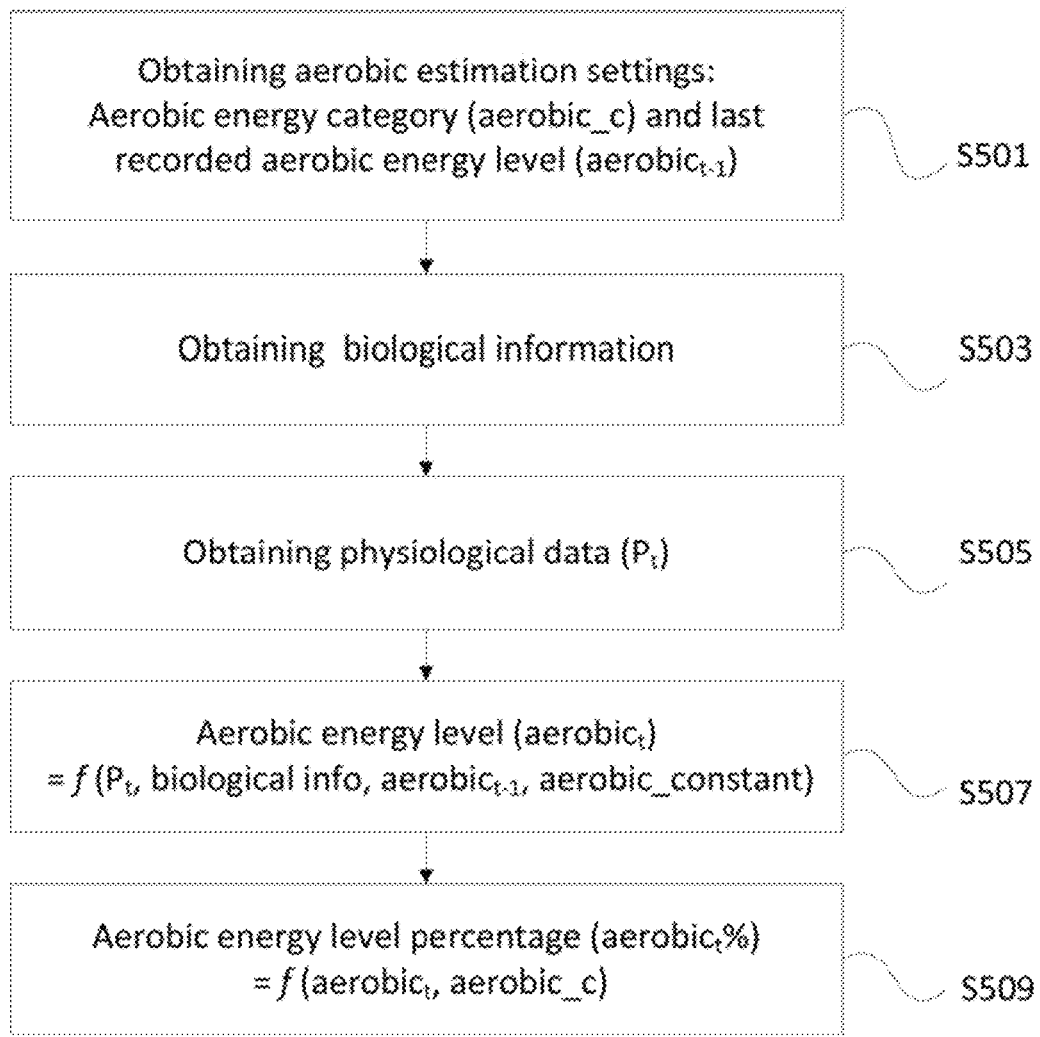
FIG. 21 is a method to estimate aerobic energy based on physiological data according to one embodiment of the present invention.

FIG. 21 is a method to estimate aerobic energy based on physiological data according to one embodiment of the present invention, wherein the method is an elaboration of the step S307 in FIG. 19.

Referring to FIG. 21, the following steps may be carried out to estimate the aerobic energy based on physiological data:

S501: Obtaining aerobic estimation settings such as aerobic energy category (aerobic_c) and last recorded aerobic energy level (aerobic$_{t-1}$) from the storage module 104;

S503: Obtaining biological information from the storage module 104;

S505: Obtaining physiological data ($P_t$) from the storage module 104;

S507: Estimating aerobic energy level (aerobic$_t$) by the processing module 102 based on the physiological data ($P_t$), the biological information, the last recorded aerobic energy level (aerobic$_{t-1}$), and an aerobic energy constant (aerobic_constant);

S509: Calculating aerobic energy level in percentage (aerobic$_t$%) of the aerobic energy category (aerobic_c) by the processing module 102 using the aerobic energy level (aerobic$_t$) and the aerobic energy category (aerobic_c).

In one embodiment of the present invention, the order of steps S501, S503 and S505 is interchangeable.

In one embodiment of the present invention, in step S505, the physiological data ($P_t$) may be measured by the sensor module 101 instead of obtained from the storage module 104. Therefore, the method to estimate aerobic energy may be carried out without relating to the method in FIG. 19.

In one embodiment of the present invention, the aerobic energy category (aerobic_c) may be an aerobic energy capacity of the user, wherein the aerobic_c may be a pre-configured value stored in the storage module 104. The higher the aerobic_c, the higher the aerobic energy capacity which means the better the user's physical endurance. Thus, the aerobic energy level in percentage estimated in step S509 may show the aerobic energy level left in percentage in comparison to the aerobic energy capacity.

In one embodiment of the present invention, the last recorded aerobic energy level (aerobic$_{t-1}$) may be stored in the storage module 104 from the last estimation of aerobic energy level, wherein aerobic$_{t-1}$ may be equal to aerobic_c in the case of first time using the exercise assistive device 100 assuming no exercise has been done by the user.

In one embodiment of the present invention, the aerobic energy constant (aerobic_constant) may be a rate of the aerobic energy consumed by an ordinary person while not exercising, wherein the rate may be a constant value pre-configured in the exercise assistive device 100. It should be noticed that, the user may consume aerobic energy all the time even when the user is asleep. Therefore, the user's aerobic energy consumption is higher than the aerobic_constant when the user is exercising, and the change of the user's aerobic energy consumption is lower than the aerobic constant when the user is recovering. In the other word, the extra aerobic energy consumption is positive when the user is exercising and negative when the user is recovering. As mentioned before in FIG. 19, the aerobic energy may be correlated to the extra calorie consumption, wherein the extra calorie consumption is the difference between the user's aerobic energy consumption and the aerobic_constant. Thus, aerobic_c minus the extra calorie consumption would be the estimated aerobic energy level (aerobic$_t$) in step S507.

Figure 22:
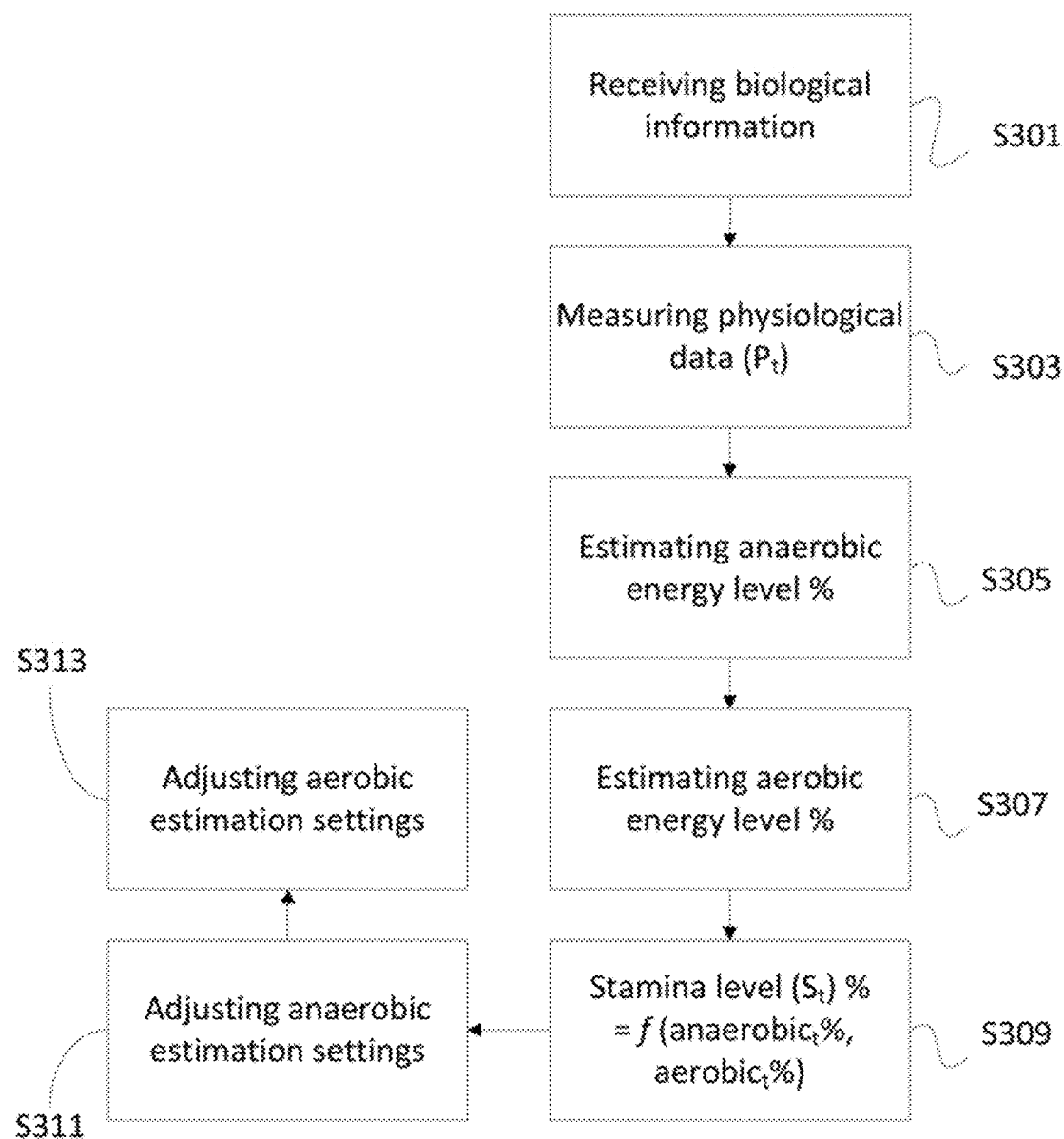
FIG. 22 is a method to estimate stamina level based on physiological data with setting adjustments according to one embodiment of the present invention.

FIG. 22 is the method to estimate stamina level ($S_t$%) based on physiological data as shown in FIG. 19 plus setting adjustments according to one embodiment of the present invention.

In one embodiment of the present invention, the method to estimate stamina level ($S_t$%) may be improved by comprising setting adjustments for anaerobic energy estimation and aerobic energy estimation, wherein the anaerobic estimation settings and aerobic estimation settings may be updated to improve the accuracy of estimating the stamina level ($S_t$%). Due to the fact that the anaerobic estimation settings and the aerobic estimation settings may not represent the actual physical condition of the user accurately each time the methods in FIG. 20~21 are carried out, the anaerobic estimation settings and the aerobic estimation settings may be updated after the estimation of anaerobic energy level and the estimation of aerobic energy level.

Referring to FIG. 22, the following steps may be carried out after the method described in FIG. 19:

S311: Adjusting the anaerobic estimation settings by the processing module 102 based on the anaerobic energy level (anaerobic$_t$);

S313: Adjusting the aerobic estimation settings by the processing module 102 based on the aerobic energy level (aerobic$_t$).

In one embodiment of the present invention, the step S311 may be carried out any time after the step S305, and the step S313 may be carried out any time after the step S307.

Figure 23:
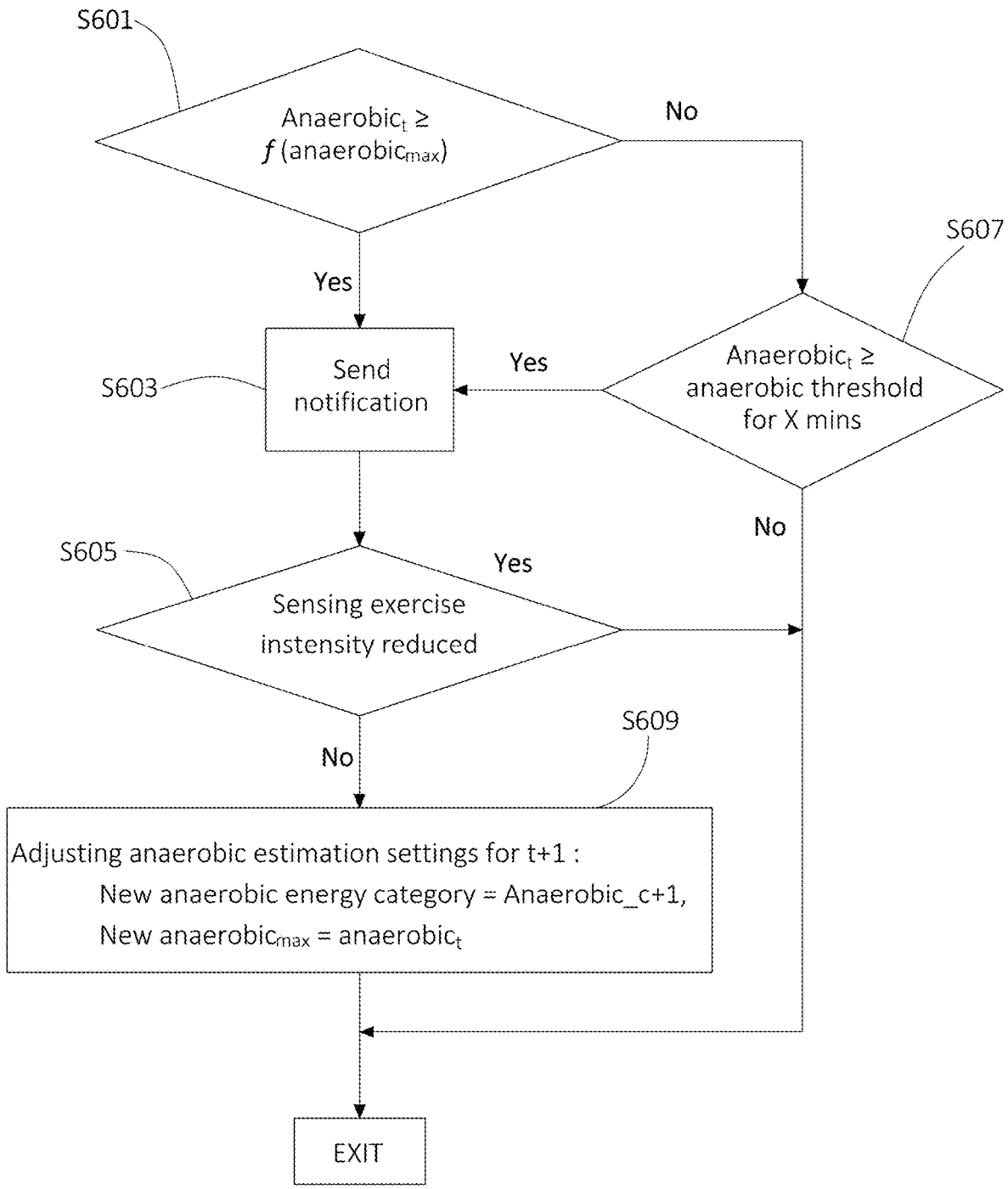
FIG. 23 is a method to adjust anaerobic estimation settings for the method to estimate stamina level according to one embodiment of the present invention.

FIG. 23 is a method to adjust anaerobic estimation settings for the method to estimate stamina level ($S_t$%) according to one embodiment of the present invention, wherein the method is an elaboration of the step S311 in FIG. 22.

Referring to FIG. 23, the following steps may be carried out to adjust anaerobic estimation settings for the method in FIG. 22:

S601: Comparing whether the anaerobic energy level (anaerobic$_t$) is larger than or equal to a function of maximum anaerobic energy $f$ (anaerobic$_{max}$) by the processing module 102, if yes go to step S603, else go to step S607;

S603: Sending a notification to the user by the user interface 103;

S605: Sensing whether the user reduces exercise intensity by the sensor module 101, if yes go to step S609, else EXIT;

S607: Comparing whether the anaerobic energy level (anaerobic$_t$) is larger than or equal to an anaerobic threshold for X minutes by the processing module 102, if yes go to step S603, else go to EXIT;

S609: Updating anaerobic estimation settings for t+1 by increasing the anaerobic energy category such as anaerobic_c+1, and the anaerobic energy level (anaerobic$_t$) will be used as new maximum anaerobic energy for next round estimation of anaerobic energy level.

In one embodiment of the present invention, the function of maximum anaerobic energy $f$ (anaerobic$_{max}$) such as $f$ (anaerobic$_{max}$)=2.5*anaerobic$_{max}$ may be pre-configured and saved in the storage module 104. Alternatively, the function of maximum anaerobic energy $f$ (anaerobic$_{max}$) may be replaced by a value configured by the user. For example the function may be replaced with a value such as 10 mmol/liter in the case when anaerobic energy level is lactate acid concentration. If the anaerobic energy level (anaerobic$_t$) estimated is 12 mmol/liter, then the exercise assistive device 100 will send a notification to the user.

In one embodiment of the present invention, the anaerobic threshold and the X minutes may be pre-configured and saved in the storage module 104. Alternatively, the anaerobic threshold and the X minutes may be configured by the user. For example, the anaerobic threshold may be 6 mmol/liter in the case when anaerobic energy level is lactate acid concentration, and the X minutes may be 5 minutes. If the anaerobic energy level (anaerobic$_t$) estimated is 7 mmol/liter for 5 minutes, then a notification will be sent to the user.

In step S609, the anaerobic_c+1 means increasing the anaerobic_c by a pre-configured amount such as a fixed value or a percentage. For example, the anaerobic_c+1 may be increasing the lactate acid dilution rate or decreasing the lactate acid production rate by 1 mmol/liter or simply by 5%. And the new maximum anaerobic energy for next round estimation of anaerobic energy level may either be the anaerobic energy level (anaerobic) or a pre-configure increment from the maximum anaerobic energy (anaerobic.).

In one embodiment of the present invention, the notification in S603 may be sent to the user in various forms such as visual, audio and vibration, etc.

In one embodiment of the present invention, in step S605, the sensor module 101 may sense whether the user reduces exercise intensity by the change of the physiological data (P$_t$). For example, the physiological data (P$_t$) sensed by the sensor module 101 is heart rate. The exercise assistive device 100 may determine the user reduces exercise intensity if the heart rate sensed at time t is lower than the previous recorded heart rate such as $P_t < P_{t-1}$.

The method to adjust anaerobic estimation settings may be applied as if the exercise assistive device 100 underestimates the user's physical strength and endurance. When the user fulfills the conditions in S601 or S607 and the exercise assistive device 100 does not sense any change in physiological data (Pt) which indicates reduction in exercise intensity, the exercise assistive device 100 adjusts the anaerobic estimation settings as shown in S609. In the case of anaerobic energy level being lactate acid concentration, the adjustments in S609 not only increases the maximum anaerobic energy but also increases the lactate acid dilution rate or decreases the lactate acid production rate for using in the next round anaerobic energy estimation as anaerobic estimation settings.

Figure 24:
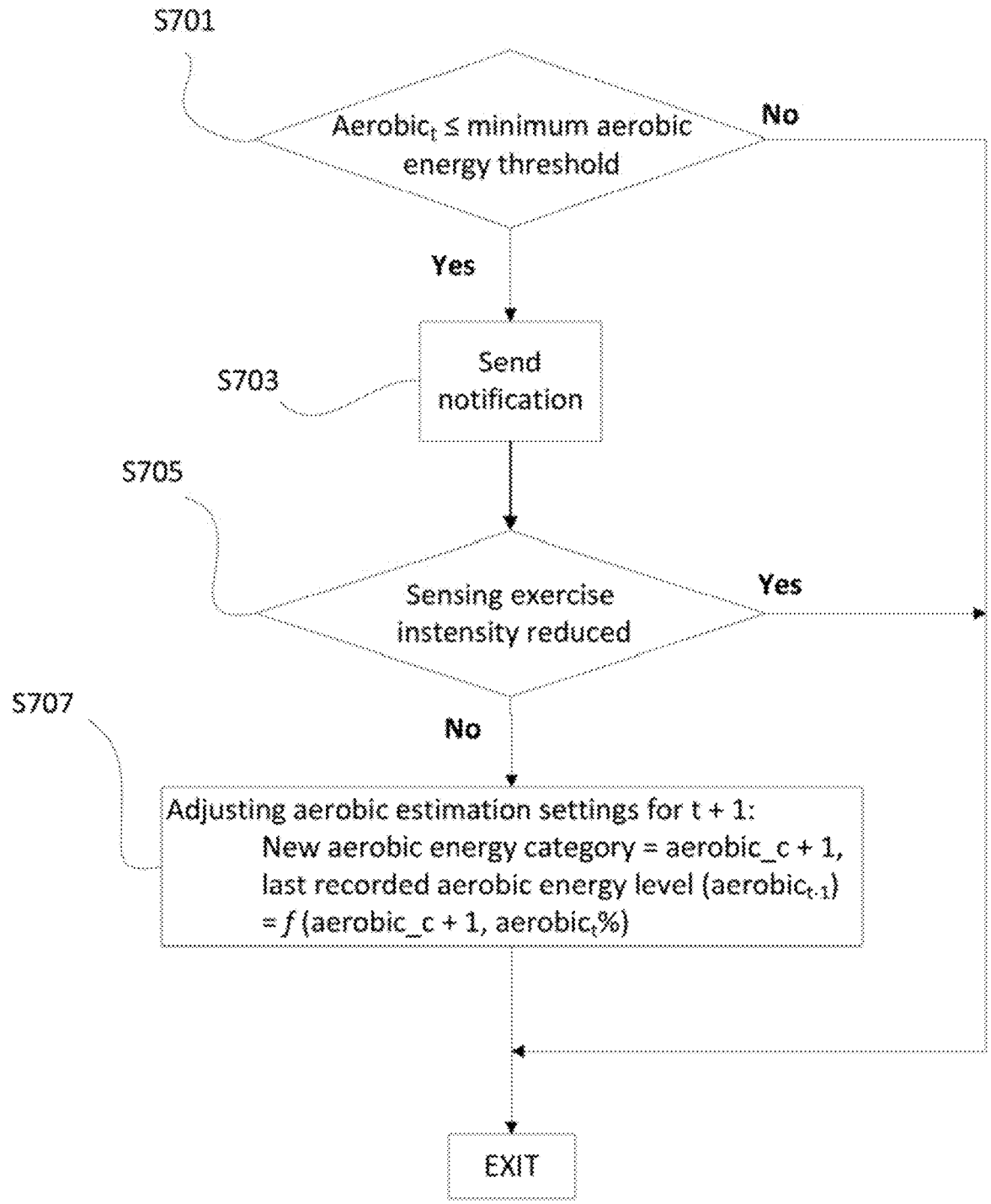
FIG. 24 is a method to adjust aerobic estimation settings for the method to estimate stamina level according to one embodiment of the present invention.

FIG. 24 is a method to adjust aerobic estimation settings for the method to estimate stamina level (S$_t$%) according to one embodiment of the present invention, wherein the method is an elaboration of the step S313 in FIG. 22.

Referring to FIG. 24, the following steps may be carried out to adjust aerobic estimation settings for the method in FIG. 24:

S701: Comparing whether the aerobic energy level (aerobic$_t$) is less than or equal to a minimum aerobic energy threshold by the processing module 102, if yes go to step S703, else EXIT;

S703: Sending a notification to the user by the user interface 103;

S705: Sensing whether the user reduces exercise intensity by the sensor module 101, if yes go to step S707, else EXIT;

S707: Adjusting aerobic estimation settings for t+1 by increasing the aerobic energy category such as aerobic_c+1, and the last recorded aerobic energy level (aerobic$_{t-1}$) will be updated as (aerobic$_{t-1}$)=f(aerobic_c+1, aerobic$_t$%).

In one embodiment of the present invention, the minimum aerobic energy threshold may be pre-configured and stored in the storage module 104. For example, the minimum aerobic energy threshold may be 5% of the aerobic_c.

In one embodiment of the present invention, the notification in S703 may be sent to the user in various forms such as visual, audio and vibration, etc.

In one embodiment of the present invention, in step S705, the sensor module 101 may sense whether the user reduces exercise intensity by the change of the physiological data (P$_t$). For example, the physiological data (P$_t$) sensed by the sensor module 101 is heart rate. The exercise assistive device 100 may determine the user reduces exercise intensity if the heart rate sensed at time t is lower than the previous recorded heart rate such as $P_t < P_{t-1}$.

In step S707, the aerobic_c+1 means increasing the aerobic_c by a pre-configure amount such as a fixed value or a percentage. For example, the aerobic_c+1 may be increasing the aerobic energy capacity by 1 or simply by 5% of aerobic_c as new aerobic energy capacity to be used in next round of aerobic energy estimation. And the last recorded aerobic energy level (aerobic$_{t-1}$) for next round estimation of aerobic energy level may be adjusted accordingly such as aerobic$_{t-1}$=the new aerobic energy capacity*aerobic$_t$%.

The method to adjust aerobic estimation settings may be applied as if the exercise assistive device 100 underestimates the user's physical strength and endurance. When the user fulfills the conditions in S701 and the exercise assistive device 100 does not sense any change in physiological data (P$_t$) which indicates reduction in exercise intensity, the exercise assistive device 100 adjusts the aerobic estimation settings as shown in S707. In the case of aerobic energy level being correlated to extra calorie consumption, the adjustments in S707 not only increases the aerobic energy capacity, which is aerobic_c, but also increases the estimated aerobic energy level accordingly, which is aerobic$_{t-1}$ for using in the next round aerobic energy estimation as aerobic estimation settings.

Figure 25:
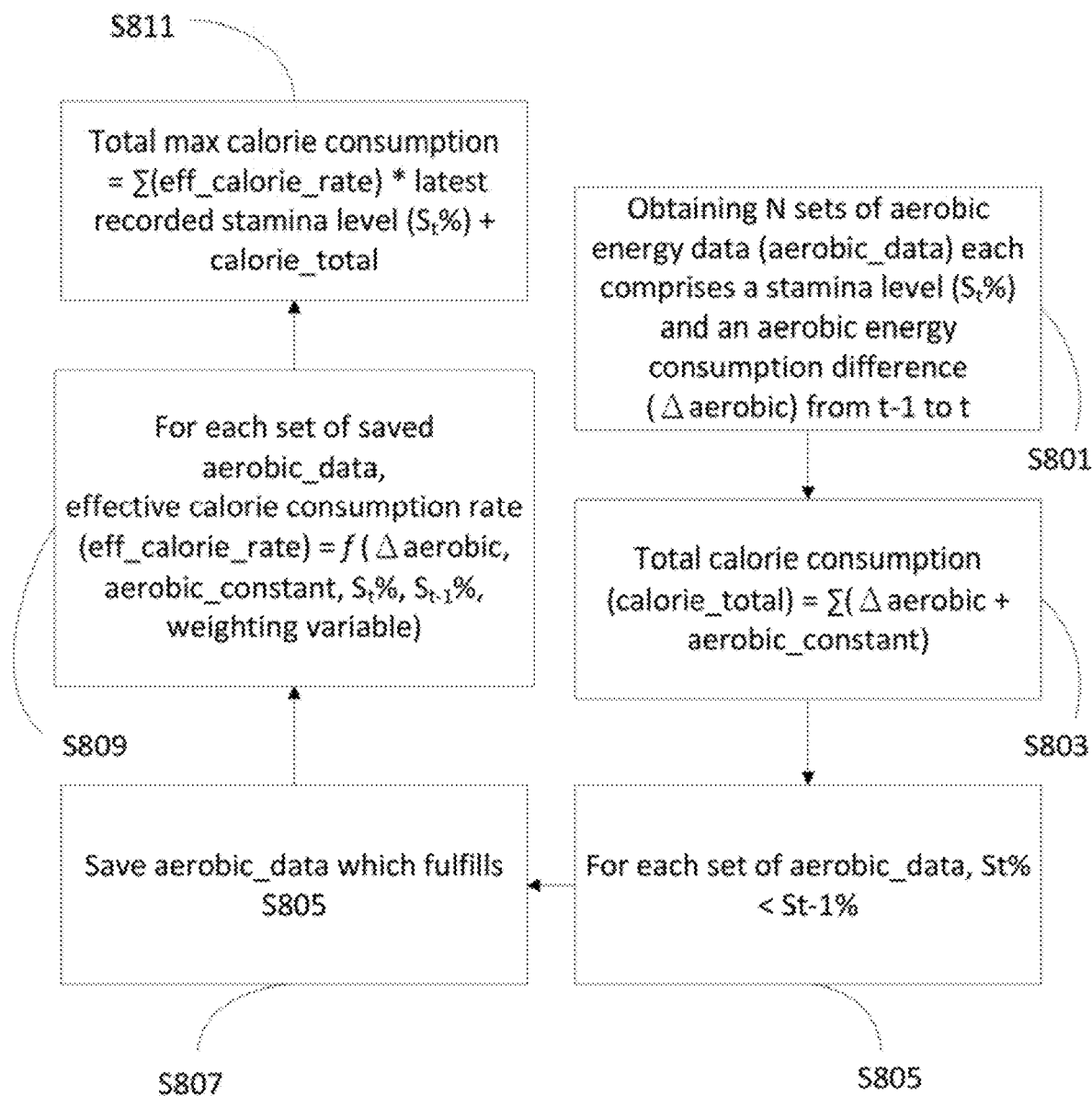
FIG. 25 is a method to estimate total maximum calorie consumption according to one embodiment of the present invention.

FIG. 25 is a method to estimate total maximum calorie consumption according to one embodiment of the present invention. As mentioned before, the aerobic energy is consumed by the user all the time, therefore the aerobic energy consumption may only increase but never decrease. As the user using the exercise assistive device 100 to monitor stamina level (S$_t$%), each of the estimation of aerobic energy level (aerobic$_t$) may be recorded together with the stamina level (S$_t$%) and saved in the storage module 104. Therefore aerobic$_{t-1}$ minus aerobic$_t$ will be an aerobic energy consumption difference (Δ aerobic). Each aerobic energy consumption difference (Δ aerobic) may be combined with the stamina level (S$_t$%) as a set of aerobic energy data (aerobic_data). As mentioned before, the aerobic energy level may be correlated to the extra calorie consumption, so the aerobic energy consumption difference (Δ aerobic) may be the difference of calorie consumption from t−1 to t. Thus, the actual calorie consumption at time t will be Δ aerobic+aerobic_constant.

Referring to FIG. 25, the following steps may be carried out by the processing module 102 and the storage module 104 to estimate the total maximum calorie consumption which the user may achieve:

S801: Obtaining N sets of aerobic energy data (aerobic_data) from the storage module 104, wherein each set of aerobic energy data (aerobic_data) comprises the stamina level (St %) and the aerobic energy consumption difference (Δaerobic) from t−1 to t;

S803: Calculating total calorie consumption (calorie_total) as a sum of all the aerobic energy consumption difference (Δaerobic) each with an aerobic_constant;

S805: For each set of aerobic_data, comparing whether the stamina level (S$_t$%) is less than the stamina level (S$_{t-1}$%) from previous set of aerobic_data;

S807: Saving all the aerobic_data which fulfills the condition in S805 in the storage module 104:

S809: For each set of saved aerobic_data, calculating effective calorie consumption rate (eff_calorie_rate) by a function of aerobic energy consumption difference (Δaerobic), aerobic_constant, stamina level ($S_t$%), previous set of stamina level ($S_{t-1}$%) and a weighting variable;

S811: Estimating the total maximum calorie consumption by Σ(eff_calorie_rate)*latest recorded stamina level ($S_t$%)+calorie_total, wherein the sum of the effective calorie consumption rate (eff_calorie_rate) for each set of saved aerobic_data from S809 is multiplied to the latest recorded stamina level ($S_t$%) of N set of aerobic_data, and adding the total calorie consumption (calorie_total) to the result of multiplication.

In one embodiment of the present invention, the step S803 may be carried out any time in between S801 and S811.

The method to estimate total maximum calorie consumption may be applied as the user would like to know how much calorie in total can be burned before the stamina level ($S_t$%) reaches zero.

In one embodiment of the present invention, in step S803, the total calorie consumption (calorie_total) may be outputted by the user interface 103, so the user may be able to keep track of the calorie consumed so far. In addition, the calorie_total may be subtracted from the total maximum calorie consumption and outputted to the user, so the user may know how much more calorie may be consumed for the usage of remaining stamina which is the latest recorded stamina level.

In one embodiment of the present invention, the calorie_total and/or the total maximum calorie consumption may be outputted to the user in various forms such as visual, audio and vibration, etc.

In one embodiment of the present invention, the weighting variable is a specific to each set of saved aerobic_data. Assuming each percent of stamina level ($S_t$%) consumption requires equal amount of time, the weighting variable may represent the contribution of aerobic energy consumption in terms of each percent of stamina level ($S_t$%) consumed by the user. For a particular set of saved aerobic_data, the contribution of calorie burning may be a ratio between an aerobic energy consumption difference (Δaerobic) from the particular set of saved aerobic_data to the sum of aerobic energy consumption difference (Δaerobic) from all the saved aerobic_data.

In one embodiment of the present invention, the effective calorie consumption rate (eff_calorie_rate) is the rate of calorie consumption when stamina is actually consumed. In the other word, eff_calorie_rate is how much calorie could be burned by the user when each percent of stamina is consumed by the user.

Figure 26:
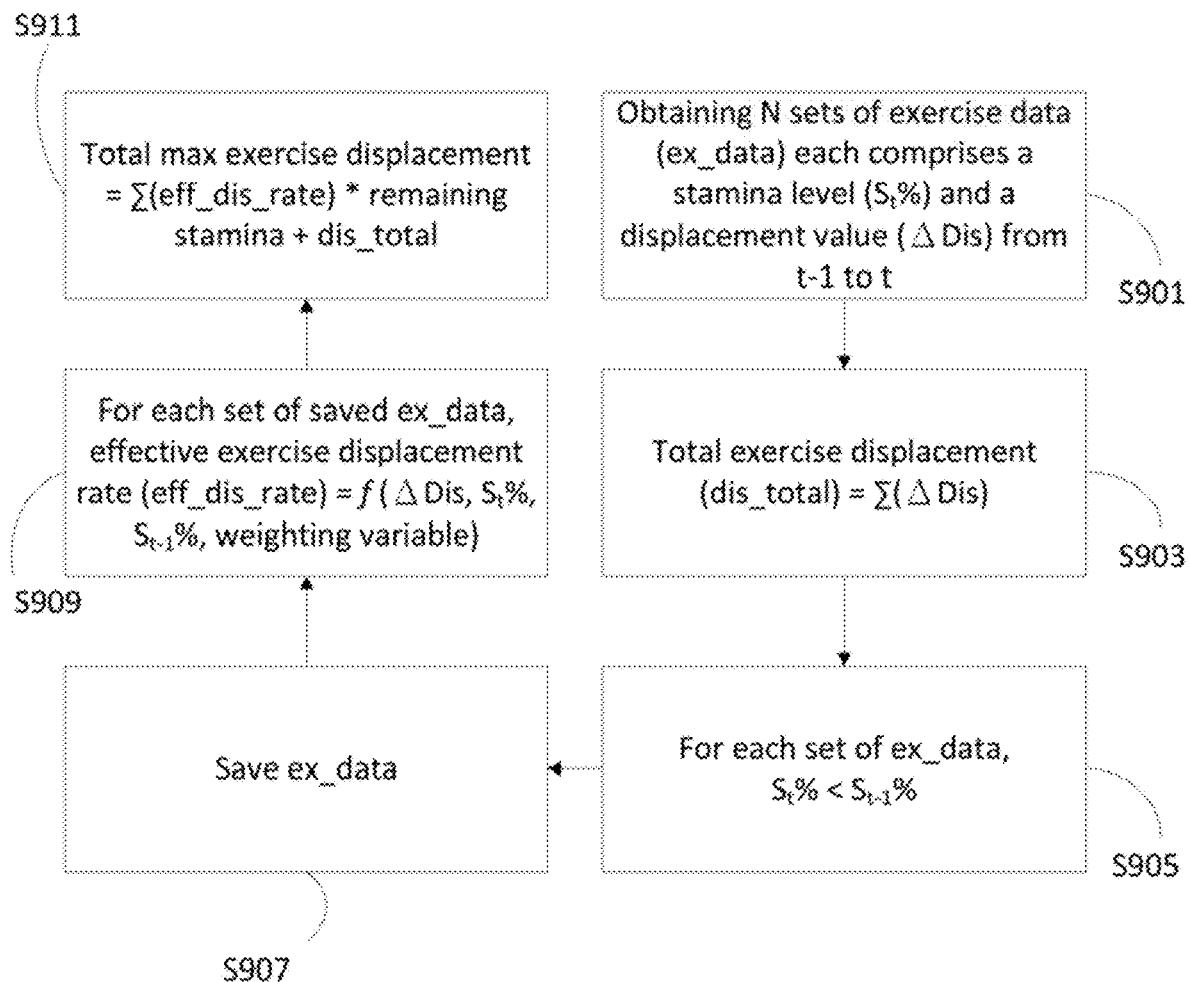
FIG. 26 is a method to estimate total maximum exercise displacement according to one embodiment of the present invention.

FIG. 26 is a method to estimate total maximum exercise displacement according to one embodiment of the present invention. As the user using the exercise assistive device 100 to monitor stamina level ($S_t$%), each of the stamina level ($S_t$%) may be recorded together with a displacement value (Δ Dis) sensed by an exercise sensor (not shown) in the sensor module 101 from t-1 to t and saved in the storage module 104. The exercise sensor may be comprised by the sensor module 101, and the exercise sensor may be one of the following: gyroscope, an accelerometer, a step counter, a cadence monitor, a speedometer, a GPS receiver, or a power meter, wherein the exercise sensor may also directly or indirectly provide real-time displacement information such as speed, elevation, inclination, etc. Each displacement value (Δ Dis) may be combined with the stamina level ($S_t$%) as a set of exercise data (ex_data). The exercise sensor may measure the user's exercising power, cadence (ex: paddling frequency, step frequency, etc), displacement information, etc.

Referring to FIG. 26, the following steps may be carried out by the processing module 102 and the storage module 104 to estimate the total maximum exercise displacement which the user may achieve:

S901: Obtaining N sets of exercise data (ex_data) from the storage module 104, wherein each set of exercise data (ex_data) comprises the stamina level (St %) and the displacement value (Δ Dis) from t-1 to t;

S903: Calculating total total exercise displacement (dis_total) as a sum of all the displacement value (Δ Dis);

S905: For each set of ex_data, comparing whether the stamina level ($S_t$%) is less than the stamina level ($S_{t-1}$%) from previous set of ex_data;

S907: Saving all the ex_data which fulfills the condition in S905 in the storage module 104;

S909: For each set of saved ex_data, calculating effective exercise displacement rate (eff_dis_rate) by a function of displacement value (ΔDis), stamina level ($S_t$%), previous set of stamina level ($S_{t-1}$%) and a weighting variable;

S911: Estimating the total maximum exercise displacement by Σ(eff_dis_rate)*latest recorded stamina level ($S_t$%)+dis_total, wherein the sum of the effective exercise displacement rate (eff_dis_rate) for each set of saved ex_data from S909 is multiplied to the latest recorded stamina level ($S_t$%) of N set of ex_data, and adding the total exercise displacement (dis_total) to the result of multiplication.

In one embodiment of the present invention, the step S903 may be carried out any time between S901 and S911.

In one embodiment of the present invention, in step S903, the total exercise displacement (dis_total) may be outputted by the user interface 103, so the user may be able to keep track of the displacement made so far. For example, distance of running, height of climbing, etc. In addition, the dis_total may be subtracted from the total maximum exercise displacement and outputted to the user, so the user may know how much more displacement may be made for the usage of remaining stamina which is the latest recorded stamina level. This is particularly useful to the user as the user may adjust exercise intensity to achieve a desire exercise displacement. For example, the user would like to cycle for 10 km. When the total maximum exercise displacement is estimated by the exercise assistive device 100 as 8 km, a notification may be sent to the user by the user interface 103. Therefore, the user may slow down to lower the rate of stamina consumption, and the user may be able to cycle more than 8 km with the remaining stamina. If the total maximum exercise displacement is estimated by the exercise assistive device 100 as 12 km, the user may increase cycling speed and still be able to achieve 10 km. In addition, the exercise assistive device 100 may calculate the rate of stamina level consumed by the user against the cycling speed of the user to suggest how fast the user may cycle and still achieve the 10 km goal. Furthermore, the exercise assistive device 100 may even calculate how many times of attack (To quickly accelerate while riding in a pack, or in smaller numbers, with a view to create a gap between the user and other cyclers) the user may make and still achieve the 10 km goal. This could be done by pre-configuring an amount of maximum exercise displacement the user needs to sacrifice to make an attack. For example, the user may use 3 km of maximum exercise displacement for each attack. When the maximum exercise displacement estimated for the user is 17 km, the user may make two more attacks and still achieve the 10 km goal without completely consuming all the stamina the user has. Alternatively, the exercise assistive device 100 may be configured to estimate the rate of stamina consumption or decrease of maximum exercise displacement while the user making an attack by tracking user's heart rate, motion, or any other exercising factors which varies with the user's exercising intensity. After calculation by the processing module 102, the available attacks may be outputted to the user by the user interface 103. Thus the user may manage his/her exercising activities with ease especially when the user does not intend to remain a constant exercising intensity.

In one embodiment of the present invention, the dis_total and/or the total maximum exercise displacement may be outputted to the user in various forms such as visual, audio and vibration, etc.

In one embodiment of the present invention, the weighting variable is a specific to each set of saved ex_data. Assuming each percent of stamina level ($S_t$%) consumption requires equal amount of time, the weighting variable may represent the contribution of displacement in terms of each percent of stamina level ($S_t$%) consumed by the user. For a particular set of saved ex_data, the contribution of displacement may be a ratio between a displacement value (ΔDis) from the particular set of saved ex_data to the sum of displacement value (ΔDis) from all the saved ex_data.

In one embodiment of the present invention, effective exercise displacement rate (eff_dis_rate) is the rate of displacement made by the user when stamina is actually consumed. In the other word, eff_dis_rate is how much displacement could be made by the user when each percent of stamina is consumed by the user.

In one embodiment of the present invention, the sensor module 101 may measure the user's exercising information such as power, cadence, speed, elevation, inclination, body composition, etc. The measurement from the sensor module 101 may be correlated with the stamina level obtained using method in FIG. 10 and FIG. 19. For example, the measurement of exercising power may be used to estimate the user's maximum power the user exerted during/after exercise via the output unit. The measurement of cadence may be used to determine whether the user is exercising efficiently or simply to provide a most efficient exercising cadence to the user via the output unit (ex: 60 steps/min for a running exercising, 60 pedals/min for a cycler, etc). The displacement information may be used to estimate how the user's body react with change of different speed, elevation, inclination, etc. Therefore, the processing module 102 may use the measurement of the exercise information to estimate the user's body endurance and/or power exertion. Furthermore, the body endurance and/or power exertion of the user may be taken into account to further adjusting the anaerobic estimation settings in FIG. 23 and/or aerobic estimation settings in FIG. 24. The body composition may be used to estimate the user's body energy density. For example, correlating the user's muscle density to anaerobic energy level, and/or aerobic energy level, and/or stamina, etc.

Previous descriptions are only embodiments of the present invention and are not intended to limit the scope of the present invention. Many variations and modifications according to the claims and specification of the disclosure are still within the scope of the claimed invention. In addition, each of the embodiments and claims does not have to achieve all the advantages or characteristics disclosed. Moreover, the abstract and the title only serve to facilitate searching patent documents and are not intended in any way to limit the scope of the claimed invention.

What is claimed is:

1. A method for calculating a stamina level of a user, and comprising:
   detecting a first exercise data of a user by a sensor for monitoring a heart rate of the user and obtaining a first physiological data corresponding to the first exercise data, wherein the first physiological data comprise a first heart rate related data, wherein the first heart rate related data is the heart rate;
   receiving a biological information from a user interface;
   determining, by a processing module, a first stamina category corresponding to the user based on the exercise data, the first physiological data, and the biological data;
   determining, by the processing module, a maximum stamina level and a minimum stamina level of the first stamina category corresponding to the use; wherein, the maximum stamina level and the minimum stamina level are based on an anaerobic energy level in percentage and an aerobic energy level in percentage; the anaerobic energy level in percentage is based on an anaerobic energy, a maximum anaerobic energy level, and a minimum anaerobic energy level; and the aerobic energy level in percentage is based on the aerobic energy level and an aerobic category corresponding to the fist physiological data;
   outputting a first stamina level on the user interface;
   detecting, by the processing module, a second exercise data and obtaining a second physiological data corresponding to the second exercise data, wherein the second physiological data comprise a second heart rate related data;
   calculating, by the processing module, a second stamina level based on the second exercise data, the second physiological data, and the first stamina level and outputting the second stamina level on the user interface; wherein the step of calculating the second stamina level comprise:
      obtaining an adjusted anaerobic energy level in percentage based on the anaerobic energy level, an adjusted maximum anaerobic energy level, and the minimum anaerobic energy level corresponding to the second physiological data;
      obtaining an adjusted aerobic energy level in percentage based on the aerobic energy level and an aerobic energy category corresponding to the second physiological data; and
      obtaining the second stamina level based on the adjusted anaerobic energy level in percentage and the adjusted aerobic energy level in percentage; and
   adjusting the first stamina category to a second stamina category corresponding to the second stamina level based on the second exercise data.

2. The method of claim 1, wherein the first exercise data comprises an activity intensity.

3. The method of claim 1, wherein the first exercise data comprises speed.

4. The method of claim 1, wherein the biological information comprises at least one of height, weight, age, and gender.

5. The method of claim 1, further comprising:
   outputting at least one parameter of heart rate, velocity, time, map, temperature, humidity, altitude, calorie consumption, exercising efficiency, power, cadence, speed, elevation, and inclination corresponding to the second exercise data on the user interface.

6. The method of claim 1, further comprising:
outputting a notification to the user corresponding to the stamina level.

7. The method of claim 1, wherein a notification is used for notifying the user to lower the exercise intensity.

8. The method of claim 1, further comprising:
mapping the second stamina level to a RPE scale and outputting the RPE scale on the user interface.

9. The method of claim 1, further comprising:
uploading a stamina level record to a social network.

10. A stamina level monitoring device, comprising:
a storage, storing a program code; and
a processor, coupled to the storage, and accessing the program code to execute:
detecting a first exercise data of a user by a sensor for monitoring a heart rate of the user and obtaining a first physiological data corresponding to the first exercise data, wherein the first physiological data comprise a first heart rate related data, the first heart rate related data is the heart rate;
receiving a biological information from a user interface;
determining a first stamina category corresponding to the user based on the exercise data, the first physiological data, and the biological data;
determining a maximum stamina level and a minimum stamina level of the first stamina category corresponding to the user; wherein, the maximum stamina level and the minimum stamina level are based on an anaerobic energy level in percentage and an aerobic energy level in percentage; the anaerobic energy level in percentage is based on an anaerobic energy, a maximum anaerobic energy level, and a minimum anaerobic energy level; and the aerobic energy level in percentage is based on the aerobic energy level and an aerobic category corresponding to the first physiological data;
outputting a first stamina level on the user interface;
detecting a second exercise data and obtaining a second physiological data corresponding to the second exercise data, wherein the second physiological data comprise a second heart rate related data;
calculating a second stamina level based on the second exercise data, second physiological data, and the first stamina level and outputting the second stamina level on the user interface; wherein the step of calculating the second stamina level comprise:
obtaining an adjusted anaerobic energy level in percentage based on the anaerobic energy level, an adjusted maximum anaerobic energy level, and the minimum anaerobic energy level corresponding to the second physiological data;
obtaining an adjusted aerobic energy level in percentage based on the aerobic energy level and an aerobic energy category corresponding to the second physiological data; and
obtaining the second stamina level based on the adjusted anaerobic energy level in percentage and the adjusted aerobic energy level in percentage; and
adjusting the first stamina category to a second stamina category corresponding the second stamina level based on the second exercise data.

11. The device of claim 10, wherein the first exercise data comprises an activity intensity.

12. The device of claim 10, wherein the first exercise data comprises speed.

13. The device of claim 10, wherein the biological information comprises at least one of height, weight, age, and gender.

14. The device of claim 10, further comprising:
outputting at least one parameter of heart rate, velocity, time, map, temperature, humidity, altitude, calorie consumption, exercising efficiency, power, cadence, speed, elevation, and inclination corresponding to the second exercise data on the user interface.

15. The device of claim 10, further comprising:
outputting a notification to the user corresponding to the stamina level.

16. The device of claim 10, wherein a notification is used for notifying the user to lower the exercise intensity.

17. The device of claim 10, further comprising:
mapping the second stamina level to a RPE scale and outputting the RPE scale on the user interface.

18. The device of claim 10, further comprising:
uploading a stamina level record to a social network.

* * * * *